US007127355B2

(12) United States Patent
Cox et al.

(10) Patent No.: US 7,127,355 B2
(45) Date of Patent: Oct. 24, 2006

(54) METHODS FOR GENETIC ANALYSIS

(75) Inventors: David Cox, Belmont, CA (US); Mark McCamish, Cupertino, CA (US)

(73) Assignee: Perlegen Sciences, Inc., Mountain View, CA (US)

(*) Notice: Subject to any disclaimer, the term of this patent is extended or adjusted under 35 U.S.C. 154(b) by 157 days.

(21) Appl. No.: 10/956,224

(22) Filed: Sep. 30, 2004

(65) Prior Publication Data
US 2005/0196770 A1 Sep. 8, 2005

Related U.S. Application Data

(60) Provisional application No. 60/590,534, filed on Jul. 22, 2004, provisional application No. 60/566,302, filed on Apr. 28, 2004, provisional application No. 60/550,662, filed on Mar. 5, 2004.

(51) Int. Cl.
*G06F 19/00* (2006.01)
*C12Q 1/68* (2006.01)

(52) U.S. Cl. .............................................. 702/20; 435/6
(58) Field of Classification Search ...................... None
See application file for complete search history.

(56) References Cited

U.S. PATENT DOCUMENTS

| 6,018,025 | A | 1/2000 | Falb et al. |
| 6,132,965 | A | 10/2000 | Austin et al. |
| 6,274,332 | B1 | 8/2001 | Keating et al. |
| 6,291,182 | B1 | 9/2001 | Schork et al. |
| 6,323,026 | B1 | 11/2001 | Keating et al. |
| 6,828,103 | B1 | 12/2004 | Herrington et al. |
| 6,872,533 | B1 | 3/2005 | Toland et al. |
| 2004/0086886 | A1 | 5/2004 | Goldstein |
| 2004/0115701 | A1 | 6/2004 | Comings et al. |
| 2004/0171056 | A1 | 9/2004 | Stanton, Jr. |
| 2005/0032066 | A1 | 2/2005 | Hang et al. |
| 2005/0037366 | A1 | 2/2005 | Gut et al. |
| 2005/0100926 | A1 | 5/2005 | Chen et al. |
| 2005/0118117 | A1 | 6/2005 | Roth et al. |

FOREIGN PATENT DOCUMENTS

| EP | 0950720 A1 | 10/1999 |
| WO | WO 01/01218 A2 | 4/2001 |
| WO | WO 02/27034 A2 | 4/2002 |
| WO | WO 02/27034 A3 | 4/2002 |

OTHER PUBLICATIONS

Zee et al. Multi-locus interactions predict risk for post-PTCA restenosis: an approach to the genetic analysis of common complex disease. The Pharmacogenomics Journal, vol. 2, pp. 197-201 (2002).*
Rothberg, Mapping a Role for SNPs in Drug Development, Nature Biotechnology, 2001, 19:209.
Zhang, Quantitative Similarity-Based Association Tests Using Population Samples, Am. J. Hum. Genet., 2001, 69:601.
Boguslavsky, Integrating Genetics Into Big Pharma, Genomics and Proteomics, Jul./Aug. 2001, p. 34.
Boguslavsky, More Ways to Use Microarrays, Genomics and Proteomics, Jul./Aug. 2001, p. 44.
Cargill, Mining for SNPs: Putting the Common Variants-Common Disease Hypothesis to the Test, Pharmcogenomics, 2000, 1:27.
Karet, Unraveling Human Diversity, Drug Discovery & Development, Nov./Dec. 2000, p. S5.
Splawski, et al., Spectrum of Mutations in Long-QT Syndrome Genes, Circulation, 2000, 102:1178.
Uhl, et al., Polysubstance Abuse-Vulnerability Genes: Genome Scans for Association, Using 1,004 Subjects and 1,494 Single-Nucleotide Polymorphisms, Am. J. Hum. Genet., 2001, 69:1290.
Judson, et al., Notes from the SNP vs. Haplotype Front, Pharmacogenomics, 2001, 2:7.
Kallioniemi, Biochip Technologies in Cancer Research, Annals of Medicine, 2001, 33:142.
Kwok, Genetic Association by Whole-Genome Analysis? Science, 2001, 294:1669.
Lai, Application of SNP Technologies in Medicine: Lessons Learned and Future Challenges, Genome Research, 2001, 11:927.
McCarthy, et al., The Use of Single-Nucleotide Polymorphism Maps in Pharmacogenomics, Nature Biotechnology, 2000, 18:505.
Menzel, Genetic and Molecular Analyses of Complex Metabolic Disorders: Genetic Linkage, Annals of the New York Academy of Sciences, 2002, 967:249-257.
Oestreicher, 4th Annual Pharmacogenomics and Medicine Lectures, Pharmacogenomics, 2001, 2:291.
Riley, et al., The Use of Single Nucleotide Polymorphisms in the Isolation of Common Disease Genes, Pharmacogenomics, 2000, 1:39.
Risch, et al., The Future of Genetic Studies of Complex Human Diseases, Science, 1996, 273:1516.
Roses, Pharmacogenetics, Human Molecular Genetics, 2001, 10:2261.
Altshuler, et al., The Common PPARgammaPro12Ala Polymorphism Is Associated with Decreased Risk of Type 2 Diabetes, Nature Genetics, 2000, 26:76.
Altshuler, et al., Guilty by Association, Nature Genetics, 2000, 26:135.
Cardon, et al., Association Study Designs for Complex Diseases, Genetics, 2001, 2:91.
Chakravarti, et al., Population Genetics -Making Scense Out of Sequence, Nature Genetics, 1999, 21:56.
Day, et al., Epidemiology & the Genetic Basis of Disease, Intl. Journal of Epidemiology, 2001, 30:661.

(Continued)

*Primary Examiner*—John S. Brusca
(74) *Attorney, Agent, or Firm*—Deana A. Arnold; Gulshan H. Shaver, Esq.

(57) ABSTRACT

Several methods are described for assessing an individual's likelihood of developing or exhibiting a multifactorial trait. The methods include determining a plurality of genotypes for the individual at a plurality of biallelic polymorphic loci, using the genotypes to compute a score for the individual, and comparing the score to at least one threshold value.

64 Claims, 1 Drawing Sheet

OTHER PUBLICATIONS

Evans, et al., Pharmacogenomics: Translating Functional Genomics into Rational Therapeutics, Science, 1999, 286:487.

Gray, et al., Single Nucleotide Polymorphisms as Tools in Human Genetics, Human Molecular Genetics, 2000, 9:2403.

Hinde, Evolution, Not Revolution, Trends in Biotechnology, 2000, 18:230.

Jorde, Linkage disequilibrium and the Search for Complex Disease Genes, Genome Research, 2000, 10:1435.

Judson, The Predictive Power of Haplotypes in Clinical Response, Pharmacogenomics, 2000, 1:15.

* cited by examiner

METHODS FOR GENETIC ANALYSIS

CROSS-REFERENCE TO RELATED APPLICATIONS

This application claims the benefit of U.S. Provisional Application No. 60/550,662, filed Mar. 5, 2004, entitled "Use of High-density Whole Genome Scanning to Select Individuals Genetically Predisposed to Adverse Events", U.S. Provisional Application No. 60/566,302, filed Apr. 28, 2004, entitled "Methods for Genetic Analysis", and U.S. Provisional Application No. 60/590,534, filed Jul. 22, 2004, entitled "Methods for Genetic Analysis", both of which are incorporated by reference herein in their entireties for all purposes.

BACKGROUND OF THE INVENTION

The DNA that makes up human chromosomes provides the instructions that direct the production of all proteins in the body. These proteins carry out the vital functions of life. Variations in the sequence of DNA encoding a protein produce variations or mutations in the proteins encoded, thus affecting the normal function of cells. Although environment often plays a significant role in disease, variations and/or mutations in the DNA of an individual are directly related to almost all human diseases, including cardiovascular, metabolic and infectious disease, cancer, and autoimmune disorders. Moreover, knowledge of genetics, particularly human genetics, has led to the realization that many diseases result from either complex interactions of several genes or their products. For example, Type I and II diabetes have been linked to multiple genes, each with its own pattern of mutations.

Additionally, knowledge of human genetics has led to a limited understanding of variations between individuals when it comes to drug response—the field of pharmocogenetics. Over half a century ago, adverse drug responses were correlated with amino acid variations in two drug-metabolizing enzymes, plasma cholinesterase and glucose-6-phosphate dehydrogenase. Since then, careful genetic analyses have linked sequence polymorphisms (variations) in over 35 drug metabolism enzymes, 25 drug targets and 5 drug transporters with compromised levels of drug efficacy or safety (Evans and Relling, *Science* 296:487–91 (1999)). In the clinic, such information is being used to prevent drug toxicity; for example, patients are screened routinely for genetic differences in the thiopurine methyltransferase gene that cause decreased metabolism of 6-mercaptopurine or azathiopurine. Yet only a small percentage of observed drug toxicities have been explained adequately by the set of pharmacogenetic markers validated to date. Even more common than toxicity issues may be cases where drugs demonstrated to be safe and/or efficacious for some individuals have been found to have either insufficient therapeutic efficacy or unanticipated side effects in other individuals.

Because any two humans are 99.9% similar in their genetic makeup, most of the sequence of the DNA of their genomes is identical. However, there are variations in DNA sequence between individuals. For example, there are deletions of many-base stretches of DNA, insertion of stretches of DNA, variations in the number of repetitive DNA elements in coding or non-coding regions, and changes in single nitrogenous base positions in the genome called "single nucleotide polymorphisms" (SNPs). Human DNA sequence variation accounts for a large fraction of observed differences between individuals, including susceptibility or resistance to disease and how an individual will respond to a particular therapeutic or treatment regimen.

Multifactorial traits, or complex traits, are influenced by multiple factors, such as genes, environmental factors, and their interactions. Often, more than one combination of genetic and/or environmental factors will result in the same multifactorial trait, and this complexity makes it difficult to determine who will develop such a trait. Further, the contribution of each factor is typically not identical to the contributions of every other factor. That is, for example, some factors may have a very strong contribution while others may have a very weak contribution. To complicate the biological basis of multifactorial traits even more, the contributions of a factor may be additive, synergistic, or completely independent from the contribution of any other factor. Some complex traits manifest common diseases, such as cardiovascular disease, diabetes, obesity, and high cholesterol. Other complex traits include such phenotypes as the way in which an individual responds to a drug or other medical treatment regimen.

In the recent past, research into the genetic basis for disease has resulted in the development of a few genetic tests for diseases. However, these genetic tests will not be useful for predicting a healthy person's probability of developing a common multifactorial disease. Many argue that genetic testing for common multifactorial traits (e.g. diseases) will not be useful in practice due to the incomplete penetrance and low individual contribution of each gene involved (Holtzman and Marteau, 2000; Vineis et al. 2001). However, these arguments are based in large part on the use of single loci to predict whether or not an individual will exhibit the trait (Beaudet 1999; Evans et al. 2001). What is needed is a reliable approach for determining an individual's risk of developing or exhibiting a multifactorial trait that is based on the individual's genotype at a plurality of loci, each of which are factors in the manifestation of the multifactorial trait.

SUMMARY

The present application discloses methods for determining an individual's risk of developing or exhibiting a multifactorial trait by determining a score for the individual based on the individual's genotype at a plurality of biallelic polymorphic loci, and comparing that score to at least one threshold value. In certain embodiments, for each of the polymorphic loci the genotype of the individual may be homozygous for an associated allele, homozygous for an unassociated allele, or heterozygous. If the individual's score is greater than a threshold value, then the individual may be considered to be at risk of developing or exhibiting the multifactorial trait, and if the individual's score is equal to or less than a threshold value then the individual may not be considered to be at risk of developing or exhibiting the multifactorial trait. If the individual's score is greater than one threshold value but less than or equal to another threshold value, then the individual may be considered to have an intermediate risk of developing or exhibiting the multifactorial trait.

The present application further discloses methods for identifying alleles of biallelic polymorphic loci that are associated with a multifactorial trait, herein referred to as "associated alleles". The methods involve performing an association study in which the genetic composition of a group of individuals who exhibit the multifactorial trait ("case group") is compared to the genetic composition of a group of individuals who do not exhibit the multifactorial trait ("control group"), and identifying as associated alleles those alleles that are significantly more prevalent in the genetic composition of the case group than the genetic composition of the control group. In certain embodiments, the associated alleles identified in a first association study with a first case group and a first control group are verified by performing a second association study with a second case group and a second control group.

The present application also discloses methods for determining a threshold value for use in a polygenic test. In one aspect, a threshold is determined by analyzing a series of risk cutoff values that are based on a set of scores from a case group and a set of scores from a control group. Determination of a threshold value involves using information including but not limited to the sensitivity, specificity, PPV, NVP, accuracy, LR+ and LR− for a polygenic test using each risk cutoff value as a threshold value; clinical data regarding the multifactorial trait, potential treatment options, and the individual being tested; and input from at least one regulatory agency.

The present invention further discloses a diagnostic or prognostic assay comprising nucleic acid probes designed to detect the associated alleles in a biological sample. In certain embodiments, the probes of the diagnostic or prognostic assay are bound to a solid substrate.

DETAILED DESCRIPTION

General

Figure 1:
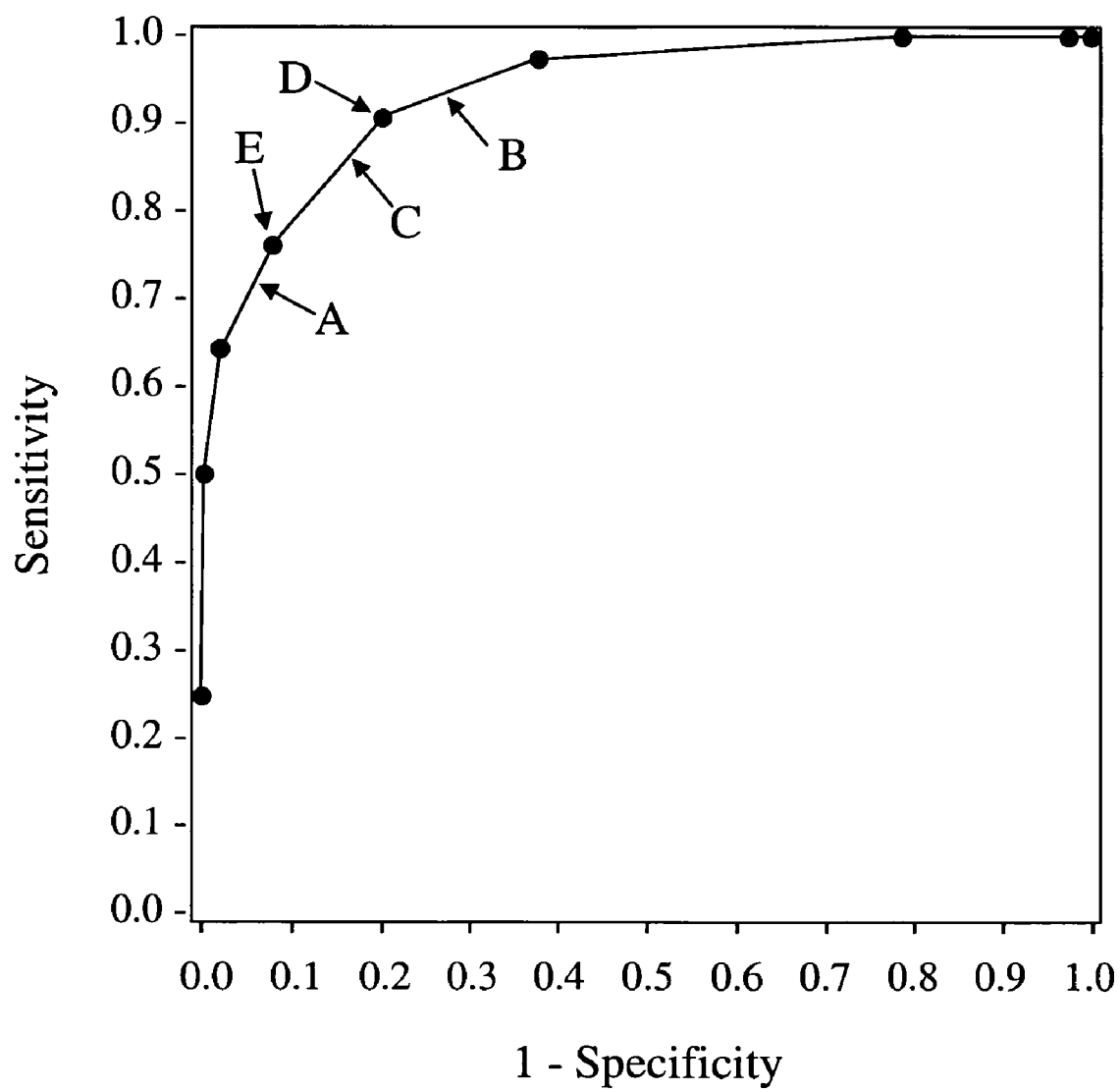
FIG. 1 illustrates an exemplary receiver operating characteristic curve for establishing a threshold value for a polygenic test.

Certain embodiments of the present invention provide methods for determining with a high degree of certainty the predisposition of an individual for developing or exhibiting a multifactorial trait, which may be, for example, development of a disease or other disorder, or a positive or negative response to a drug. This determination is based on the genotype of the individual at a plurality of genetic loci, each of which is a genetic factor involved in the manifestation of the multifactorial trait. The methods further provide the benefit of making such a determination without the knowledge of the degree to which, or the way in which, each genetic factor influences the manifestation of the multifactorial trait. The methods of the invention instead rely on the cumulative effects of multiple genetic factors and enable one of skill to make an accurate prediction of an individual's likelihood of developing or exhibiting the multifactorial trait based on the genotype of the individual at a plurality of genetic loci that have been determined to be associated with the incidence of the multifactorial trait.

Multifactorial traits are influenced by a plurality of genetic factors, environmental factors, and interactions between them. Further, the contribution of each factor is typically not identical to the contributions of every other factor. That is, for example, some factors may have a strong contribution while others may have a weak contribution. To complicate the biological basis of multifactorial traits even more, the contributions of a factor may be additive, synergistic, or completely independent from the contribution of any other factor. Methods presented herein do not rely on the magnitudes of the effect that each factor has on the multifactorial trait, nor do they depend on whether the effects of the factors are additive, synergistic or independent. In other words, the methods do not require that the magnitude of each factor's effect be taken into consideration when calculating the an individual's "risk" (e.g. probability, likelihood) of developing such a multifactorial trait. In addition, the methods don't require knowledge of environmental factors that may influence the multifactorial trait. Instead, the methods presented herein rely on a set of assumptions that the individual contribution of each genetic factor is the same as every other genetic factor's contribution, that the individual contributions are simply additive across all genetic factors underlying the multifactorial trait, and that the risk of an individual may be assessed in the absence of knowledge of the contribution of environmental factors to manifestation of the multifactorial trait.

Certain embodiments of the present invention provide methods for performing an association study to identify a set of polymorphic loci associated with a multifactorial trait. Also provided are methods for determining which of the set of associated polymorphic loci to include in a polygenic test for the multifactorial trait, as well as means to determine certain characteristics of such a test, e.g., sensitivity, specificity, positive predictive value, negative predictive value, relative risk, likelihood ratio, accuracy, etc. Further provided are methods for using a set of associated polymorphic loci in a polygenic test to determine the predisposition of an individual for developing or exhibiting that multifactorial trait. In one embodiment, the multifactorial trait is a disease and individuals identified as likely to develop that disease may be subjected to treatments or other medical interventions to treat or prevent development of the disease. In another embodiment, the methods of the present invention are used to predict the efficacy of a proposed medical treatment, wherein if the treatment is unlikely to be efficacious then it is not administered to a patient. In another embodiment, the multifactorial trait is the exhibition of an adverse event in response to a drug treatment. Individuals identified as likely to exhibit the adverse event may be excluded from the drug treatment regimen or if treated with the drug (e.g. as a last resort) additional monitoring may be utilized in anticipation of the adverse event. In still further embodiments, methods disclosed herein are used for drug development, and specifically to increase the efficacy and safety of drugs by selecting appropriate patients for inclusion in studies.

As will be readily apparent to one of skill in the art, the methods of the present invention are to be used as tools to aid in the identification of individuals who have or are at risk of developing a multifactorial trait of interest, and that the methods presented herein may be used in conjunction with clinical information regarding the trait, individual(s) being tested, and the population from which the individual(s) is selected, as well as other clinical tests and even the clinical "intuition" of the practitioner. Genetic tests are typically used to assist clinicians, not to rule clinical decision-making. Essentially, it is the clinician who must determine how to use a diagnostic or prognostic test using, for example, clinical knowledge of the trait (e.g. disease) and the potential treatment options, the characteristics of the diagnostic test, the population with which the test was developed, and the specific patient being tested, while balancing the risks to individuals incorrectly identified by the test and the benefits to individuals correctly identified. In another aspect, a clinician may also consider the risks to individuals incorrectly identified as "positive" by the test as compared to the risks to individuals incorrectly identified as "negative" by the test (e.g., does withholding treatment to a patient in need of such treatment cause more harm than administering treatment to a patient who does not need it?)

Reference will now be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention.

Association Studies

In one aspect of the present invention, a set of polymorphic loci associated with the manifestation of a multifactorial trait and the associated alleles that correspond to those polymorphic loci are identified by carrying out an association study, and the associated alleles are further used to determine if an individual who is not a member of the case or control groups is genetically predisposed to developing or exhibiting the multifactorial trait. A multifactorial trait may be any type of phenotypic trait, such as exhibition of, susceptibility to, or resistance to a disease or other medical disorder, a response to a drug or other medical treatment regimen, or another physical or mental characteristic. For example, in one embodiment the multifactorial trait is a disease and an association study compares the genetic composition of a group of individuals who exhibit the disease (cases) with the genetic composition of a group of individuals who do not exhibit the disease (controls). Examples of diseases that are multifactorial include, but are not limited to asthma and other pulmonary diseases, psoriasis, dyslexia, infertility, gout, cataracts, obesity, diabetes, gastrointestinal disorders, cancer, cardiovascular disease, stroke, hypertension, attention deficit disorder, schizophrenia, manic depression, osteoporosis, immune system disorders, multiple sclerosis, atherosclerosis, and epilepsy. Certain developmental abnormalities are also included in this category, such as cleft lip/palate, congenital heart defects and neural tube defects. In another embodiment the multifactorial trait is a response to a drug and an association study compares the genetic composition of a group of individuals who exhibit a particular response to the drug (cases) with the genetic composition of a group of individuals who do not exhibit the particular response (controls). In one aspect, the drug response may be related to the efficacy of the drug. For example, the drug may be highly efficacious for individuals in the case group and have poor efficacy for individuals in the control group, or vice versa. In another aspect, the drug response may be related to an adverse event in response to administration of the drug. For example, the individuals in the case group may exhibit an adverse event in response to the drug and the individuals in the control group may not exhibit the adverse event. Although various examples are provided herein that describe uses of the methods of the present invention in combination with specific multifactorial traits, these examples are not intended to limit the scope of the invention, which encompasses use of the methods presented herein in conjunction with any multifactorial trait whose manifestation involves a plurality of genetic loci.

Typically, at least 50, and preferably at least 100 individuals are in both of the case and control groups. In some studies, there are at least 200, or at least 500 individuals in at least one of the case and control groups. Often, there are more individuals in the control group than in the case group. In certain embodiments, the individuals in the case and control groups are mammals, but the case and control groups may also comprise nonmammalian individuals such as, for example, bacteria, fungi, protists, viruses, archaeans, and other eukaryotes such as reptiles, amphibians, fish, birds, crustaceans, insects, and plants. In some embodiments the individuals in the case and control groups are humans.

Typically, the composition of the case and control groups should be similar with regards to characteristics aside from the multifactorial trait under consideration. For example, in one embodiment, similar numbers of men and women of similar ages will be selected for each group. In certain embodiments, an environmental risk factor may influence the composition of the case and control groups. For example, only smokers (or only nonsmokers) may be selected to comprise the case and control groups for a study on lung cancer. In some embodiments of the present invention, membership of the case and control groups is adjusted so that the population structures of the two groups are "matched" prior to performing an association study. Population structure (or "population stratification") refers to the heterogeneity of the genetic composition of individuals within a population. For example, the population structure of a case group that is composed mainly of Italians is different than a control group that is composed mainly of Mexicans due to the different ethnic origins of the two groups. If an association study was performed without matching the groups, then genetic loci that are associated with an Italian ancestry, but not with Mexican ancestry may erroneously appear to be associated with the multifactorial trait under study. By matching the population structure of the case and control groups, one of skill can control for the genetic differences between the case and control groups that are not related to the multifactorial trait of interest. Therefore, the genetic differences between the groups that are identified by the subsequent association study are more likely to be loci that are causally-related to the multifactorial trait of interest. Methods for matching case and control groups prior to performing an association study are described in detail in U.S. utility patent application Ser. No. 10/427,696, filed Apr. 30, 2003, entitled "Method for Identifying Matched Groups"; and U.S. provisional patent application No. 60/497,771, filed Aug. 26, 2003, entitled "Matching Strategies for Genetic Association Studies in Structured Populations".

Nucleic acid samples are collected from the individuals in the case and control groups for use in genotyping assays. The nucleic acid samples may be DNA or RNA and may be obtained from various biological samples such as, for example, whole blood, semen, saliva, tears, fecal matter, urine, sweat, buccal, skin and hair. In certain aspects, the nucleic acid samples comprise genomic DNA. Sample nucleic acids may be prepared for analysis using any technique known to those skilled in the art. Preferably, such techniques result in the production of a nucleic acid molecule sufficiently pure to determine the presence or absence of one or more polymorphisms at one or more locations in the nucleic acid molecules. Such techniques are commonly known and may be found, for example, in Sambrook, et al., *Molecular Cloning: A Laboratory Manual* (Cold Spring Harbor Laboratory, New York) (2001), and Ausubel, et al., *Current Protocols in Molecular Biology* (John Wiley and Sons, New York).

One or more nucleic acids of interest may be amplified and/or labeled before determining the presence or absence of one or more polymorphisms in the nucleic acid. Any amplification technique known to those of skill in the art may be used in conjunction with certain methods of the present invention including, but not limited to, polymerase chain reaction (PCR) techniques. PCR may be carried out using materials and methods known to those of skill in the art. See generally PCR Technology: *Principals and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Matilla et al., *Nucleic Acids Res.* 19: 4967 (1991); Eckert et al., *PCR Methods and Applications* 1: 17 (1991); PCR (eds. McPherson et al., IRL Press, Oxford); and U.S. Pat. No. 4,683,202. Other suitable amplification methods include the ligase chain reaction (LCR) (see Wu and Wallace, *Genomics* 4: 560 (1989) and Landegren et al., *Science* 241: 1077 (1988)), transcription amplification (Kwoh et al., *Proc. Natl. Acad. Sci. USA* 86: 1173 (1989)), self-sustained sequence replication (Guatelli et al., *Proc. Nat. Acad. Sci. USA*, 87: 1874 (1990)) and nucleic acid-based sequence amplification (NASBA). Further, the methods disclosed in pending U.S. patent application Ser. No. 10/106,097, filed Mar. 26, 2002, entitled "Methods for Genomic Analysis"; Ser. No. 10/042,406, filed Jan. 9, 2002, entitled "Algorithms for Selection of Primer Pairs"; Ser. No. 10/042,492, filed Jan. 9, 2002, entitled "Methods for Amplification of Nucleic Acids"; Ser. No. 10/236,480, filed Sep. 5, 2002, entitled "Methods for Amplification of Nucleic Acids"; Ser. No. 10/174,101, filed Jun. 17, 2002, entitled "Methods for Storage of Reaction Cocktails"; Ser. No. 10/447,685, filed May 28, 2003, entitled "Liver Related Disease Compositions and Methods", Ser. No. 10/768,788, filed Mar. 4, 2004, entitled "Apparatus and Methods for Analyzing and Characterizing Nucleic Acid Sequences"; and Ser. No. 10/427,696, filed Apr. 30, 2003, entitled "Method for Identifying Matched Groups" are suitable for amplifying, labeling, or further manipulating (i.e. fragmentation) nucleic acids for use in certain methods of the present invention.

In an association study, genetic loci that are known to be polymorphic (e.g. SNPs) are genotyped for each individual in each of the case and control groups and a relative allele frequency is calculated for each of the loci for each of the groups based on the genotypes present in the groups. That is, if ten polymorphic loci are genotyped, then twenty relative allele frequencies are determined, ten for each of the case and control groups. For a given polymorphic locus, the relative allele frequency for the case group is compared to that for the control group, and if the polymorphic locus has a significantly different relative allele frequency in the case group than in the control group it is identified as a locus that may be associated with the multifactorial trait that distinguishes the case and control groups ("associated locus"). In certain embodiments, a significant difference in relative allele frequency is a difference of greater than about 5%, or greater than about 8%, or greater than about 10%, or greater than about 12%, or greater than about 15%. The allele that is present more often in the case population may be referred to as the "associated allele", and the allele that is present more often in the control population may be termed the "unassociated allele". The number of associated loci (and, hence, associated alleles for biallelic associated loci) identified will vary widely depending on how many polymorphic loci contribute to the multifactorial trait (e.g. disease) under study or are in linkage disequilibrium with loci that contribute. For example, if the manifestation of a disease involves ten genes, then the number of associated loci identified will be dependent on how many of the polymorphic loci that are genotyped in the association study are in linkage disequilibrium with the alleles of the ten genes that cause the disease. Typically, the number of loci involved in the manifestation of a multifactorial trait ranges between about five to several hundred, but it may be higher or lower. For a detailed description of methods for performing an association study using relative allele frequencies of a case and a control group, see U.S. patent application No. 60/460, 329, filed Apr. 3, 2003, and Ser. No. 10/768,788, filed Jan. 30, 2004, both of which are entitled "Apparatus and Methods for Analyzing and Characterizing Nucleic Acid Sequences".

Genotyping of the individuals may be performed using any technique known to those of skill in the art. Preferred techniques permit rapid, accurate determination of multiple variations with a minimum of sample handling. Some examples of suitable techniques involve but are not limited to direct DNA sequencing, capillary electrophoresis, hybridization, allele-specific probes or primers, single-strand conformation polymorphism analysis, nucleic acid arrays, bead arrays, restriction fragment length polymorphism analysis, cleavase fragment length polymorphism analysis, random amplified polymorphic DNA, ligase detection reaction, heteroduplex or fragment analysis, differential sequencing with mass spectrometry, atomic force microscopy, pyrosequencing, FRET (e.g., TaqMan (Applied Biosystems, Inc., Foster City, Calif.) and Molecular Beacon (Stratagene, La Jolla, Calif.) assays), and other techniques well known in the art. Several methods for DNA sequencing are well known and generally available in the art. See, for example, Sambrook, et al., *Molecular Cloning: A Laboratory Manual* (Cold Spring Harbor Laboratory, New York) (2001); Ausubel, et al., *Current Protocols in Molecular Biology* (John Wiley and Sons, New York) (1997), Twyman, et al. (2003) "Techniques Patents for SNP Genotyping", *Pharmacogenomics* 4(1): 67–79; and Kristensen, et al. (2001). "High-Throughput Methods for Detection of Genetic Variation", *BioTechniques* 30(2):318–332. For details on the use of nucleic acid arrays (DNA chips) for the detection of, for example, SNPs, see U.S. Pat. No. 6,300,063 issued to Lipshultz, et al., and U.S. Pat. No. 5,837,832 to Chee, et al., HuSNP Mapping Assay, reagent kit and user manual, Affymetrix Part No. 90094 (Affymetrix, Santa Clara, Calif.).

The relative allele frequency for a case or control group may be determined directly, by individually genotyping all the individuals in the population to determine the exact amount of each allele in each individual in the population. Methods for individually genotyping a plurality of individuals are described in detail in U.S. patent application Ser. No. 10/351,973, filed Jan. 27, 2003, entitled "Apparatus and Methods for Determining Individual Genotypes" and U.S. patent application Ser. No. 10/786,475, filed Feb. 24, 2004, entitled "Improvements to Analysis Methods for Individual Genotyping". Alternatively, pooled genotyping may be used to determine a relative allele frequency for each of the case and control groups. For pooled genotyping, nucleic acid samples from the case group are pooled together (case pool) and nucleic acid samples from the control group are pooled together (control pool), and the relative allele frequencies for the case group and the control group are determined through analysis of the case and control pools. Methods for pooled genotyping are discussed in detail in U.S. patent application No. 60/460,329, filed Apr. 3, 2003, and Ser. No. 10/768,788, filed Jan. 30, 2004, both of which are entitled "Apparatus and Methods for Analyzing and Characterizing Nucleic Acid Sequences".

Genetic Loci

The term "SNP" or "single nucleotide polymorphism" refers to a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway (http://genome.ucsc.edu/cgi-bin/hgGateway) or the NCBI dbSNP website (http://www.ncbi.nlm.nih.gov/SNP/), or may be experimentally determined as described in U.S. patent application Ser. No. 10/106,097, filed Mar. 26, 2002, entitled "Methods for Genomic Analysis"; and Ser. No. 10/284,444, filed Oct. 31, 2002, entitled "Human Genomic Polymorphisms". Although the use of SNPs is described in some of the embodiments presented herein, it will be understood that other biallelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele", and the other allele may be referred to as "the unassociated allele". Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include derivatives of DNA such as amplicons, RNA transcripts, cDNA, DNA analogs, etc. The polymorphic loci that are screened in an association study may be in a diploid or a haploid state and, ideally, would be from sites across the genome.

In some embodiments of the present invention, an association study involves screening at least about 100 SNPs, or at least about 500 SNPs, or at least about 1000 SNPs, or at least about 10,000 SNPs, or at least about 100,000 SNPs, or at least about 1,000,000 SNPs. In certain embodiments, SNPs that are located in one or more parts of the genome believed to be associated with the multifactorial trait are screened. In other embodiments, SNPs on one or more chromosomes are screened. In still further embodiments, SNPs from every chromosome in a genome are screened. In other embodiments, multiple SNPs from every chromosome in a genome are screened. In other embodiments, SNPs that are located in the coding region or the regulatory region of a gene are screened. In further embodiments, SNPs that have been found to be associated with the differential allelic expression of a gene are screened. (Differential allelic expression occurs when one allele of a gene is expressed at a higher level than another allele of the same gene in a heterozygote, and is described in detail in U.S. patent application Ser. No. 10/438,184, filed May 13, 2003, entitled "Allele-specific Expression Patterns".) In certain embodiments, all known SNPs (approximately 3 million to date) are screened. In other embodiments, a subset of SNPs is screened that may be used to predict the allelic composition of a subset of SNPs that is not screened. SNPs screened by the methods presented herein may be in either a diploid or a haploid state in an individual.

The number of associated SNPs (and therefore associated alleles) identified by the methods presented herein is dependent on several criteria. First, it is dependent on the number of genetic loci that are involved in the manifestation of the disease. For example, if the genetic basis for a multifactorial disease involves only a few loci, then the number of associated SNPs and associated alleles will typically be less than that found for a multifactorial disease whose genetic basis involves hundreds of loci. Further, the number of associated SNPs and associated alleles identified is dependent on how many SNPs are screened in the association study. For example, an association study that screens only one hundred SNPs in the case and control groups will be less likely to find a large number of associated SNPs than one that screens one million SNPs. Typically, the methods presented herein will identify between about ten and several hundred associated SNPs/associated alleles, but may identify more or fewer.

Validation of the Set of Associated Alleles

In one embodiment, to validate the identification of the associated alleles, the association study is repeated using a second case and second control population. This second association study determines whether those associated alleles from the first association study are still identified as associated alleles based on the relative allele frequencies of a new set of cases and controls, and those that do "replicate" have thereby been validated as associated SNPs. In certain embodiments, the polymorphic loci that were screened in the first association study are also screened in the second validating association study. In other embodiments, a subset of the polymorphic loci that were screened in the first association study are screened in the second validating association study. In a specific embodiment, the set of polymorphic loci screened in the second association study comprises the associated polymorphic loci that were identified by the first association study. For example, if 30,000 SNPs are identified as associated with the incidence of a disease in a first association study, then those 30,000 SNPs are subsequently screened in a second association study for which a second case group of individuals exhibiting the disease and a second control group not exhibiting the disease are selected. In certain embodiments, the second case group is selected according to the same criteria as the first case group, and the second control group is selected according to the same criteria as the first control group. In one aspect, the first and second case group and the first and second control group have no members in common. The second association study may be performed using a pooled or individual genotyping methodology.

In other aspects, if an association study is performed using pooled genotyping, the set of associated alleles determined by the pooled genotyping methodology may be validated by individually genotyping the set of associated SNPs in every individual in the case and control groups and recalculating and recomparing the relative allele frequencies. The associated alleles that were identified based on the initial pooled genotyping analysis that have a significantly higher allele frequency in the case group as compared to the control group based on the individual genotyping data are thereby verified as associated alleles. This validation step may be performed for a first association study that utilizes a pooled genotyping methodology, or may be performed for a second validating association study that uses a pooled genotyping methodology.

More than one validation method may be used in a study design to identify a set of associated SNPs. For example, in one embodiment of the present invention, an initial association study is performed with a case population of individuals that exhibit a disease and a control population of individuals that do not exhibit the disease. A pooled genotyping methodology is used to genotype the case and control groups at approximately 1.5 million SNP loci to identify about 30,000 SNPs with relative allele frequencies that differ significantly between the case and control groups. In a next validating step, the case and control groups are individually genotyped at each of the about 30,000 SNPs identified in the "pooled" association study to identify approximately 300 SNPs that have significantly different relative allele frequencies in the case group than in the control group based on the individual genotyping methodology. Thus, these approximately 300 SNPs have been validated by individual genotyping. In a further validating step, a second association study is performed in which the approximately 300 SNPs validated by the individual genotyping step are further validated by performing a second association study based on an individual genotyping methodology with a second case group and a second control group. Those SNPs that replicate in the second association study are classified as associated SNPs for the disease, and the alleles of the associated SNPs that are more abundant in the case groups than in the control groups are termed the associated alleles.

Use of Associated Alleles for Determining Risk Cutoffs

In one embodiment of the present invention, the genotypes of the individuals in the case and control groups at each of the disease-associated SNP loci are used to develop a series of cutoff values to be used in determining the predisposition of an individual for developing the multifactorial trait that distinguishes the case group from the control group.

In one aspect, the genotypes at each associated SNP location are collected for all the individuals in the case and control groups. If individual genotyping was performed during the association study, as discussed supra, then the genotyping data collected for the associated SNP positions during the association study may be used. However, if individual genotypes have not been determined, then each member of the case and control group must be individually genotyped for the set of associated SNPs. For example, in the case of a biallelic SNP, a diploid individual may have one of three different genotypes, homozygous for the associated allele, homozygous for the unassociated allele, and heterozygous (having one associated allele and one unassociated allele). The methods presented herein may also be applied to haploid organisms, or to haploid loci in diploid organisms (e.g., Y chromosome loci in humans). For a haploid locus, there would be only two genotypes, one for each possible allele.

In another aspect, each individual in the case and control groups is assigned a score based on their genotype at each of the associated SNP loci. Each associated allele is valued at one point so each SNP genotype that is homozygous for the associated allele is worth two points, each SNP genotype that is heterozygous is worth one point, and each SNP genotype that is homozygous for the unassociated allele is worth zero points. In one embodiment for a haploid locus, each SNP genotype with the associated allele is worth one point and each SNP genotype with the unassociated allele is worth zero points. In another embodiment for a haploid locus, each SNP genotype with the associated allele is worth two points and each SNP genotype with the unassociated allele is worth zero points. For a given individual, all the points across all the associated SNPs are summed to provide a score for that individual. For example, if 100 associated SNPs are being genotyped, then the maximum score for an individual is 200, meaning that the individual has two associated alleles at every associated SNP position. In other words, the individual is homozygous for the associated allele at every SNP location. The minimum score is 0, for an individual that has no associated alleles at any associated SNP positions, or is homozygous for the unassociated allele at every SNP location. Scores are calculated for every individual in the case and control groups. For example, 100 associated SNPs were examined for a case population of 102 individuals and a control population of 405 individuals. The lowest score in the case group was 42 and the highest score was 97; for the control group, the lowest score was 23 and the highest score was 79.

In another aspect, a series of risk cutoff values is determined. Risk cutoff values represent hypothetical threshold values for use in a genetic test to identify individuals likely to develop or exhibit a multifactorial trait. For example, individuals who have a score higher than a threshold value may be diagnosed as being likely to exhibit the multifactorial trait, and those who have a score at or lower than the threshold may be diagnosed as being unlikely to exhibit the multifactorial trait. Alternatively, multiple thresholds may be used to determine an individual's risk of exhibiting the multifactorial trait.

The series of risk cutoff values spans a range from 1 to the highest score calculated for an individual in the association study, regardless of whether they were a member of the case or control group. In one example, the highest score for an individual was 97 points, so the range from which the risk cutoff values were determined (the risk cutoff range) was between 1 and 97. In certain aspects, risk cutoff values are selected from across the risk cutoff range, although the selection of particular risk cutoff values is somewhat arbitrary. In some embodiments, every score within the risk cutoff range is chosen. In other embodiments, every $n^{th}$ score (every $5^{th}$ or $10^{th}$, for example) is chosen. In still further embodiments, the range is divided into percentages and every $n^{th}$ percentage is chosen. In some embodiments, more risk cutoff values are selected from the middle portion of the complete range of scores than at the top or bottom portions of the range, or vice versa. For example, in the case in which the complete range of scores was between 1 and 97, risk cutoff values were chosen at every 10th score between 20 and 80, and additional risk cutoff values of 55 and 65 were added to better assess the middle of this range (see Table 1).

In a subsequent step, each of the risk cutoff values is compared to the scores calculated for the individuals in the case and control groups. Specifically, the scores for the case ("affected") and control ("unaffected") individuals are used to determine which of the risk cutoff values provides the best sensitivity, specificity, positive predictive value (PPV), negative predictive value (NPV), accuracy or a combination thereof for distinguishing individuals likely to exhibit the multifactorial trait from those not likely to exhibit the multifactorial trait, thereby identifying a risk cutoff value that would be a good threshold value for a polygenic test using the associated SNPs. In addition, identification of an appropriate threshold value may further involve use of clinical information (e.g. regarding the multifactorial trait, population under study, or individuals being tested) and/or interaction of the practitioner of the present invention with an outside agency (e.g. U.S. Food and Drug Administration (FDA)). This threshold value may be developed into a genetic test, e.g. a diagnostic, with the sensitivity, specificity, PPV, NPV and accuracy calculated based on the threshold value and the scores for the case and control group individuals.

A two-class genetic test has two possible results. A positive test result indicates that an individual exhibits or is likely to exhibit a trait of interest and a negative test result indicates that an individual does not exhibit and is not likely to exhibit the trait of interest. As such, the reliability of a genetic test is related to how often the result of the test correctly identifies an individual as "positive" or "negative" for the trait. True positives (TP) and true negatives (TN) are test results that accurately identify individuals as positive (e.g. "affected") and negative (e.g. "unaffected"), respectfully. A false positive (FP) is a test result that incorrectly classifies an individual as a positive when they are in fact negative for the trait. Likewise, a false negative (FN) is a test result that incorrectly classifies an individual as a negative when they are in fact positive for the trait. Measures of TP, TN, FP and FN are used to calculate the sensitivity, specificity, PPV and NPV for a genetic test.

The "sensitivity" of a test is a measure of the ability of the test to correctly identify an affected individual, or an individual who will develop the trait of interest. The closer the sensitivity is to one, the more accurate the test is in identifying affected individuals. Specifically, the sensitivity refers to the proportion of affected individuals who are correctly diagnosed as such by the test, and is calculated as the number of individuals correctly identified as affected (TP) divided by the total number of affected individuals (TP+FN). A high sensitivity is preferred so that most affected individuals are identified as such by the genetic test. The "specificity" of a test is a measure of the ability of the test to correctly identify an unaffected individual, or an individual who will not develop the trait of interest. The closer the specificity is to one, the more accurate the test is in identifying unaffected individuals. Specifically, the specificity refers to the proportion of unaffected individuals who are correctly identified as such by the test, and is calculated as the number of individuals correctly identified as unaffected (TN) divided by the total number of unaffected individuals (TN+FP). A high specificity is preferred so that the number of individuals who are incorrectly identified as affected is minimized. Thus, for a given risk cutoff value, the sensitivity is calculated as the proportion of case individuals with a score higher than the risk cutoff value, and the specificity is calculated as the proportion of control individuals with a score lower than or equal to the risk cutoff value (or, one minus the proportion of control individuals with a score higher than the risk cutoff value).

The "positive predictive value" (PPV) of a genetic test assesses the reliability of a positive test outcome/result, and is computed as the proportion of people with a positive test result who actually have the trait of interest. In other words, it is the probability that a positive test result accurately identifies an individual who has the trait, and is calculated as the number of individuals correctly identified as affected (TP) divided by the total number of individuals identified as affected by the genetic test (TP+FP). In many cases, a high PPV is preferred so that most individuals who are identified as affected are actually affected. For example, a PPV of 0.98 means that an individual with a positive test result has a 98% chance of having or developing the trait. The "negative predictive value" (NPV) of a genetic test assesses the reliability of a negative test outcome/result, and is computed as the proportion of people with a negative test result who do not have the trait of interest. Put another way, it is the probability that a negative test result accurately identifies an individual who does not have the trait, and is calculated as the number of individuals correctly identified as unaffected (TF) divided by the total number of individuals identified as unaffected (TN+FN). A high NPV is sometimes preferred so that most individuals who are identified as unaffected are actually unaffected (e.g., in excluding subjects at risk for adverse events associated with the administration of a specific drug). For example, an NPV of 0.999 means that an individual with a negative test result has only a 0.1% chance of having or developing the trait (e.g., of experiencing the adverse event in response to the drug). Thus, for a given risk cutoff value, the PPV may be calculated as the proportion of all individuals with a score higher than the risk cutoff value that are actually in the case group, and the NPV is calculated as the proportion of all individuals with a score lower than or equal to the risk cutoff value that are actually in the control group.

The prevalence of a trait is the frequency of the trait among the population being tested, and is calculated as the number of existing cases divided by the total population at a given point in time. Although the sensitivity and specificity of a test are not influenced by the prevalence of the trait under consideration, both PPV and NPV are highly influenced by the prevalence of the trait in the population being tested; a lower disease prevalence results in a lower PPV and a higher NPV. Both PPV and NPV may also be calculated as a function of the sensitivity (sens), specificity (spec) and prevalence (prev):

$$PPV=(sens)(prev)/[(sens)(prev)+(1-spec)(1-prev)]$$

$$NPV=(spec)(1-prev)/[(spec)(1-prev)+(1-sens)(prev)].$$

Threshold values may also be selected using likelihood ratios for the genetic test. A likelihood ratio (LR) is a way to incorporate the sensitivity and specificity of a test into one measure, and gives an indication of how much the odds of having or developing a given trait change based on a positive or negative test result. Since sensitivity and specificity are fixed characteristics of the test itself, the LR is independent of the prevalence of the trait in the population, unlike PPV and NPV. An LR is the likelihood that a given test result would be expected in an individual with the trait compared to the likelihood that the same result would be expected in an individual without the trait. An LR for a positive test result (LR+) provides a measure of how much the odds of an individual having or developing the trait increase when the test is positive, and is calculated as the sensitivity divided by (1−specificity). The better test to use for "ruling in" a trait is the one with the largest LR+. An LR for a negative test result (LR−) provides a measure of how much the odds of an individual having or developing the trait decrease when the test is negative, and is calculated as (1−sensitivity) divided by the specificity. The better test to use to "rule out" a trait is the one with the smaller LR−. LRs of greater than 10 or less than 0.1 are usually judged to be of high diagnostic value. The LRs are combined with the "pre-test odds" to determine the "post-test odds" that the individual tested has or will develop the trait of interest (post-test odds=pre-test odds×LR). The pre-test odds are computed with information about the prevalence of the trait, the characteristics of the population and information about the particular individual being tested, and represent the likelihood that the individual will have or develop the trait prior to testing. The post-test odds represent the likelihood that the individual will have or develop the trait given the testing results. In one embodiment of the present invention, a threshold value is selected that maximizes the LR for a genetic test.

Yet another measure of the value or utility of a genetic test is the accuracy, which measures the overall agreement between the test results and the actual disease state. Accuracy is calculated as the sum of the true positives and true negatives divided by the total number of sample results ((TP+TN)/(TP+TN+FP+FN)). The accuracy of a genetic test may be used to determine which of a set of risk cutoff values may be a useful threshold value in a polygenic test.

Sensitivity, specificity, PPV, NPV and accuracy are calculated for each risk cutoff value, and Table 1 below lists these values for an example in which 102 cases and 405 controls were analyzed. The cutoff values chosen from the complete range of scores are shown in the first column. The number of case individuals with a score higher than the corresponding cutoff value is shown in the second column. The third column lists the number of control individuals with a score higher than the corresponding cutoff value. The sensitivity for a test using of each of the corresponding cutoff values as threshold values is shown in the fourth column. The specificity for a test using of each of the corresponding cutoff values as threshold values is shown in the fifth column. The PPV and NPV of a test using each of the corresponding risk cutoff values as threshold values are shown in the sixth and seventh columns, respectively. Finally, the accuracy of a test using each of the corresponding cutoff values as threshold values is shown in the eighth column.

TABLE 1

| Risk Cutoff Values | # Cases (out of 102) | # Controls (out of 405) | Sensitivity | Specificity | PPV | NPV | Accuracy |
|---|---|---|---|---|---|---|---|
| 80 | 25 | 0 | 0.25 | 1 | 1 | 0.84 | 0.85 |
| 70 | 51 | 2 | 0.50 | 0.995 | 0.96 | 0.89 | 0.90 |
| 65 | 65 | 8 | 0.64 | 0.98 | 0.89 | 0.91 | 0.91 |
| 60 | 79 | 34 | 0.77 | 0.92 | 0.70 | 0.94 | 0.89 |
| 55 | 93 | 81 | 0.91 | 0.80 | 0.53 | 0.97 | 0.82 |
| 50 | 99 | 154 | 0.97 | 0.62 | 0.39 | 0.99 | 0.69 |
| 40 | 102 | 318 | 1 | 0.21 | 0.24 | 1 | 0.37 |
| 30 | 102 | 394 | 1 | 0.03 | 0.21 | 1 | 0.22 |
| 20 | 102 | 405 | 1 | 0 | 0.20 | 1 | 0.20 |

Under optimum conditions a genetic test is both highly sensitive and high specific with a high PPV, NPV and accuracy so that all individuals tested are correctly identified as having or not having the trait of interest. However, in typical circumstances the selection of an optimal risk cutoff value may be based, e.g., on the best combination of specificity, sensitivity, PPV, NPV and accuracy, or a subset thereof. As shown in Table 1, using a high risk cutoff value increases the specificity and PPV of the test while lowering the sensitivity and NPV. Therefore, if a genetic test to determine the predisposition of an individual for developing a disease is based on a high risk cutoff value, very few individuals would be misdiagnosed as having a high risk of developing the disease, but a large proportion of those that do have a high risk would not be identified. On the other hand, using a low risk cutoff value increases the sensitivity and NPV while lowering the specificity and PPV whereby although most or all individuals at high risk would be identified as such, a significant number of individuals at low risk would also be erroneously identified as being at high risk. Therefore, it is apparent that neither of these extremes is useful, but instead a balance of sensitivity, specificity, PPV and NPV may be determined for the particular trait, population and individual under consideration.

Determination of a threshold value is dependent on many factors. For example, clinical knowledge of the disease is typically required to make this determination. Further, a threshold value for a polygenic test may be regulated by a regulatory agency (e.g. FDA) or varied by a clinician depending on, for example, information regarding the potential treatments, characteristics of the polygenic test, or the specifics for a particular patient. Further, a threshold value may or may not be used in a dichotomous fashion. For example, an individuals treatment may vary depending on whether the individual's score is greater than the threshold value (e.g. administer a drug) or less than or equal to the threshold value (e.g. don't give the drug). Alternatively, individual's with scores close to the threshold may be treated differently than those with scores far from the threshold. For example, a decision may be made by a clinician to administer the drug to an individual with a score that is slightly below the threshold based on additional factors, such as clinical knowledge and input from the individual. Further, the use of "greater than" versus "less than or equal to" with regards to comparing a score to a threshold value is merely a matter of convention, and in alternative embodiments of the present invention the use of "greater than or equal to" versus "less than" may be used instead, as will be clear to one of ordinary skill in the art.

In one aspect, determining a threshold value is dependent on the severity of the disease. For example, if the trait relates to the development of a severe disease, then one would prefer to have a very high sensitivity despite a lower specificity since identifying those at high risk is critical for those individuals. For example, treatable malignancies (in situ cancers or Hodgkin's disease) should be found early, so sensitive tests should be used in the diagnostic work-up. Similarly, a test with a high NPV is preferred for a severe disease to ensure that the number of false negatives is low. Since the number of false positives may be significant due to a less than ideal PPV, additional testing may be performed to confirm the status of those individual who tested positive/affected, using, e.g., a highly accurate "gold standard" test. As such, it may be more acceptable to have a lower PPV when there are other confirmatory diagnostics readily available. For example, the rate of atypical cervical cells in the general population is approximately 1/1000 and the sensitivity and specificity of a pap test are 0.70 and 0.90, respectively. Based on these values, the PPV and NPV for the pap test are 0.00696 and 0.999, respectively, meaning that a person with a positive pap test has only a very small likelihood of truly having atypia, while a person with a negative pap test almost certainly is disease-free.

In certain aspects, a high specificity and PPV is preferred for a genetic test, e.g. when there are highly undesirable repercussions for false positive test results. For example, if the test is being used to make a decision on whether an individual will receive a dangerous treatment regimen (transplant surgery, chemotherapy, radiation, drug with serious adverse events, mastectomy, etc.), then it is important that individuals who are identified by the test as needing the treatment actually do need the treatment. For example, a genetic test may be developed for identification of individuals who are at high risk of death in the absence of a heart transplant procedure. Thus, individuals who have a score higher than a threshold value are identified as likely to die unless they receive a new heart. Such a test would be preferred to have a very high PPV (~1.0) so that only individuals with a high probability of death are considered for a heart transplant. Although this would mean that a significant number of individuals that will die without a heart transplant will be excluded from the treatment (lower NPV), optimally no individuals will be given a heart transplant who do not absolutely need one.

Another factor in determining an appropriate threshold value for a genetic test is the prevalence of the disease in the population as a whole. For example, take a trait that is extremely rare in the population. A specificity of 0.95 may seem acceptably high, but it means that five percent of individuals who do not have a high risk will be misdiagnosed as having a high risk of developing the trait. Thus, for a trait that has a frequency in the population of 1/10,000, approximately 500 individuals would be misdiagnosed as "high risk" (false positives) for every individual that is correctly identified as being at risk of developing the trait. Accordingly, it is best suited to use a cutoff with a higher specificity for rare, non-severe traits and a cutoff with a higher sensitivity for common, severe traits. Further, as described above, PPV and NPV are highly dependent on the prevalence of the trait of interest. For example, the PPV of a genetic test used to identify individuals at risk of developing a disease from a population that has a low prevalence of the disease will be lower than the PPV of the same genetic test used to identify individuals at risk of developing the disease from a population that has a high prevalence of the disease. Similarly, the NPV of a genetic test used to identify individuals at risk of developing a disease from a population that has a low prevalence of the disease will be higher than the NPV of the same genetic test used to identify individuals at risk of developing the disease from a population that has a high prevalence of the disease. As such, although a genetic test may have a very high PPV (or a very high NPV) when being used to test individuals in one population, it may not be useful in other populations where the prevalence of the trait of interest is different, and therefore a different threshold value may be chosen for different populations depending on the prevalence of the trait of interest. In short, one skilled in the art can select threshold values to achieve one or more clinically useful parameters, such as sensitivity, specificity, PPV, NPV, accuracy, and the like for a patient population having a particular prevalence for a given trait using not only the methods presented herein, but also clinical knowledge and intuition, as well as, e.g., interactions with regulatory agencies such as the FDA.

In one aspect of the present invention, a threshold value for a polygenic test using the associated SNPs is determined using a ROC (receiver operating characteristic) curve (Hanley et al. (1982) *Radiology* 143:29–36; and Beck, et al. (1986) *Arch. Pathol. Lab. Med.* 110:13–20) based on the sensitivities and specificities calculated for the risk cutoff values. A ROC curve is related to the inherent tradeoff between the sensitivity and specificity of a genetic test, and is generated by plotting the sensitivity as a function of one minus the specificity for each risk cutoff value, as shown in FIG. 1, which illustrates a ROC curve generated using the data from Table 1. Thus, each risk cutoff value corresponds to a "data point" on the ROC curve. The area under the curve provides a measure of the reliability of the genetic test. For a genetic test that can perfectly distinguish between affected and unaffected individuals (sensitivity and specificity are each 1), the area under the curve is 1. For a genetic test that fails to distinguish between affected and unaffected individuals, the area under the curve is 0.5. In general, the closer the curve follows the left-hand and top borders of the plot, the more accurate the genetic test, and the closer the curve comes to the 45 degree angle of the ROC space, the less accurate the test. Computer programs commonly used for analyzing ROC curves are publicly available and include ROCKIT, CORROC2, LABROC4, ROCFIT, CLABROC, ROCPWR, LABMRMC, and PROPROC, all of which may be downloaded from Kurt Rossman Laboratories for Radiological Image Research at the following website: www-radiology.uchicago.edu/krl/KRL_ROC/software_index .htm#ROC%20calculations%20Auxiliary%20software. In certain embodiments, a threshold value is chosen from the risk cutoff values whose data points are found in a portion (e.g. percentage) of the ROC curve that is nearest the upper left corner of the plot. For example, if data points were chosen from the 20% of the ROC curve nearest the upper left corner of the plot shown in FIG. 1 (between arrows A and B), then a threshold value would be selected from the data points corresponding to risk cutoff values of 55 and 60, indicated as D and E, respectively. In other embodiments, a threshold value is determined to be the risk cutoff value whose sensitivity and specificity is represented by the data point nearest the upper left corner of the plot. In FIG. 1, this data point (D) corresponds to a risk cutoff value of 55. In still further embodiments, a threshold value is determined from the location on the ROC curve that is closest to the upper left corner of the plot. In FIG. 1, this location is indicated as C, and corresponds to a sensitivity of about 0.87 and a specificity of about 0.84. In this embodiment, a risk cutoff value is determined that corresponds to the sensitivity and specificity represented by this location on the curve, and that risk cutoff value is used as the threshold value for a genetic test using the associated SNPs. For example, since the location C is between the data points D and E, the optimal risk cutoff value to use as a threshold value must be between 55 and 60. To determine the optimal risk cutoff value, the sensitivity and specificity are determined for all risk cutoff values in that range based on the scores of the case and control groups (see Table 2). The risk cutoff value whose sensitivity and specificity are closest to 0.87 and 0.84, respectively, is chosen, and in this example that risk cutoff value is 56, with a sensitivity of 0.88 and a specificity of 0.84. Therefore, 56 is chosen as the threshold value for a polygenic test using the associated alleles.

In another embodiment of the present invention, a threshold value may be chosen based on a specific desired clinical result. For example, a genetic test may be developed to stratify patient population as a means for reducing the incidence of adverse events in individuals given a particular therapeutic. For example, a drug may be approved for limited use due to a 4% incidence of adverse events, but could be approved for wider use if the incidence of adverse events was lowered by at least 50%. In this example, "cases" are individuals that would have the adverse event in response to the drug and "controls" are individuals who would not have the adverse event when exposed to the drug. The risk that an individual will experience the adverse event is determined by computing a score for the individual based on their genotypes at a set of associated loci, and then e.g. comparing the score to a threshold value for a genetic test, where the threshold was determined by analysis of the PPV, NPV, sensitivity, specificity, etc., or some combination thereof for a genetic test based on the scores of a case group and a control group. For example, individuals with a number of associated alleles higher than a threshold value may be identified as being at high risk of having the adverse event. Using a threshold value of 60 would eliminate 77% of cases and 8% of controls. Since the incidence of adverse events is known to be 4%, a patient population of 1000 would have ~40 cases, about 31 (77%) of which would have >60 associated alleles and about 9 of which would have ≦60 associated alleles. The same patient population would have ~960 controls, about 77 (8%) of which would have >60 associated alleles and about 883 of which would have ≦60 associated alleles. After excluding the 108 individuals with ≦60 associated alleles, the incidence of an adverse event in the 892 individuals that were not excluded may be computed: (9/892)×100=1%. The incidence of an adverse event in the individuals that were excluded can be similarly computed: (31/108)×100=29%. Using the same computational methods, risk cutoff values of 59 and 61 were also evaluated as threshold values for the diagnostic test. A risk cutoff value of 59 resulted in a predicted incidence of the adverse event in the individuals that were not excluded from treatment of 1%, but more individuals in the control group were excluded (92), meaning that more individuals not at risk of the adverse event would be denied treatment with the drug if this risk cutoff value were used as a threshold value in a diagnostic test. A risk cutoff value of 61 resulted in a predicted incidence of the adverse event in the individuals that were not excluded from treatment of 1.2%, which is higher than that for a risk cutoff value of 60, however fewer control individuals were excluded (69), meaning that more individuals not at risk of the adverse event would be able to benefit from the drug treatment if this risk cutoff value were used as a threshold value in a diagnostic test. Further, if a practitioner wanted to maximize the number of controls that were treated while keeping the risk of adverse events at or below 2% in the treated population, a threshold value of 69 would exclude only 10 of the control individuals and would provide a treated population with a risk of the adverse event at 2%. Further, as shown in Table 2, for the test to identify enough cases for removal from the group of patients to be treated to bring the risk of the adverse event down to 2% need only be 0.53. Therefore, using the risk cutoff value of 69 as a threshold value in such a diagnostic test would decrease the incidence of adverse events in the population of individuals treated by the particular therapeutic, thereby improving its risk/benefit profile and allowing it to broaden its label, while maximizing the total number of individuals who are not at risk of the adverse event that will be included in the treatment. Clearly, the choice of a particular risk of adverse events in the treated population is an important factor is determining a thereshold value for such a diagnostic test, and the determination of that level of risk must be determined by the clinician in concert with any regulatory agencies that would be involved in the approval of such a diagnostic (e.g. FDA). For example, if a 1% risk of adverse event was desired, a threshold value of 60 could be chosen, which would increase the NPV of the test (thereby reducing the actual number of adverse events in the treated population) while sacrificing PPV (more individuals who could benefit (controls) would be excluded). Patients who are excluded could be treated differently, e.g. with a different drug, or could be given the drug along with close monitoring for the adverse event, or with another treatment or agent that would counteract the adverse event.

TABLE 2

| Risk Cutoff Values | # Cases (out of 102) | # Controls (out of 405) | Sensitivity | Specificity | PPV | NPV | Accuracy |
|---|---|---|---|---|---|---|---|
| 69 | 54 | 4 | 0.53 | 0.99 | 0.93 | 0.89 | 0.90 |
| 61 | 74 | 29 | 0.73 | 0.93 | 0.72 | 0.93 | 0.89 |
| 60 | 79 | 34 | 0.77 | 0.92 | 0.70 | 0.94 | 0.89 |
| 59 | 80 | 39 | 0.78 | 0.90 | 0.67 | 0.94 | 0.88 |
| 58 | 81 | 44 | 0.79 | 0.89 | 0.65 | 0.95 | 0.87 |
| 57 | 86 | 53 | 0.84 | 0.87 | 0.62 | 0.96 | 0.86 |
| 56 | 90 | 64 | 0.88 | 0.84 | 0.58 | 0.97 | 0.85 |
| 55 | 93 | 81 | 0.91 | 0.80 | 0.53 | 0.97 | 0.82 |

The concepts of sensitivity, specificity, PPV, NPV, accuracy, likelihood ratios, and ROC curves, and methods of choosing an appropriate threshold value for a diagnostic test are widely used and well known to those of skill in the art (see, for example, Janssens, et al. (2004) Am. J. Hum. Genet. 74:585–588; www.bamc.amedd.army.mil/DCI/articles/dci10972.htm; Baum M. (1995) Lancet 346:436–437; Forrest P. (1990) "Breast Cancer: the decision to screen"; Nuffield Provincial Hospitals Trust; Morrison, A. S. (1985) "Screening in Chronic Disease" Oxford University Press Inc. USA; www.genome.gov/10002404; med.usd.edu/som/genetics/curriculum/1ITEST7.htm; Bauman A. (1990) Australian Prescriber 13:62–64; Walker et al. (1986) Med. J. Aust. 145:185–187; Gilbert R. (2001) Western J. Med. 174:405–409; Frohna, J. G. (2001) "Fostering the Efficient, Effective Use of Evidence-based Medicine in the Clinic", $2^{nd}$ edition, University of Michigan; Raglans, R. A. (2000) "Studying a Study and Testing a Test", $4^{th}$ edition, Lippincott Williams & Wilkins; www.cebm.net/likelihood_ratios.asp; and www1.elsevier.com/gej-ng/10/22/71/52/140/article.html). For example, in one study the best threshold value for serum alpha-fetoprotein to discriminate between liver cirrhosis and hepatocellular carcinoma was evaluated based on the area under a ROC curve, likelihood ratios, sensitivity, specificity, PPV and NPV (Soresi et al. (2003) Anticancer Res. 23(2C):1747–1753). In other study, mammography, sonography, and MR mammography were compared to determine if one or a combination of two or more of these techniques would provide the best results for detection of invasive cancer and multifocal disease using the measures of sensitivity, specificity, PPV, NPV and accuracy (Malur et al. (2001) Breast Cancer Res. 3:55–60). The combination of all three imaging techniques led to the best results with a sensitivity of 0.994, a specificity of 0.953, a PPV of 0.939, an NPV of 0.996 and an accuracy of 0.97. In yet another study, the area under ROC curves for two clinical tests was compared to determine whether one of the tests or a combination of both of the tests was most accurate at identifying the class of a breast lesion (Buscombe et al. (2001) J. Nuc. Med. 42(1):3–8). In another study, it was found that prostate-specific antigen (PSA) testing for detecting prostate cancer had a sensitivity of 0.86 and a specificity of 0.33 for a cutoff of 4 ng/ml of PSA, but that lowering the cutoff to 2 ng/ml of PSA increase the sensitivity to 0.95, but lowered the specificity to 0.20 (Hoffman, et al. (2002) BMC Fam. Pract. 3(1):19). Once all risk cutoff values are examined and their respective specificities, sensitivities, PPVs, NPVs, LR+ and LR− values, and accuracies (or some subset thereof) are calculated, an optimal balance between these parameters, or some subset thereof, may be used in the determination of a threshold value. One skilled in the art may choose a threshold value that optimizes any of these measures, or a combination thereof, to achieve a clinically useful means of stratifying a patient population for e.g. diagnosis, prognosis, pharmacogenomics, drug development, theranostics and the like.

In certain embodiments of the present invention, more than one threshold value may be determined and used to classify an individual's risk of exhibiting a multifactorial trait. In one such embodiment, a first threshold value chosen may be based on optimization for sensitivity, which will reduce the number individuals who are at high risk but are not identified by the test (false negatives). Individuals that test "positive" in a genetic test using the first threshold value are then subjected to the same genetic test using a second threshold value that may be based on optimization for specificity. This second threshold value will reduce the number of individuals who test positive but who are not really at high risk (false positives). Using two such threshold values sequentially may serve to increase the accuracy of the method.

Another embodiment of the present invention in which more than one threshold value is determined and used to classify an individual's risk of exhibiting a multifactorial trait is one in which a plurality of threshold values are used simultaneously in the same genetic test. In such a test, an individual's risk is determined based on which threshold values the individual's score was greater than, less than, or equal to. In one embodiment at least about two thresholds are used, or at least about five thresholds are used or at least about 10 thresholds are used. In certain embodiments, every possible score for a given polygenic test is used as a threshold; in other embodiments a subset of possible scores is used, wherein said subset may encompass a specific range of scores or may include scores chosen from across the entire range of scores. For example, a first threshold may be chosen such that individuals that have a score higher than the first threshold are classified as highly likely to develop a disease and are therefore treated with an appropriate drug to prevent onset. A second threshold may be chosen such that individuals that have a score lower than the second threshold are classified as having a very low likelihood of developing the disease and are therefore not treated to prevent onset. Those individuals with a score that is between the first and second thresholds may be classified as having an intermediate likelihood of developing the disease and may therefore be treated differently than individuals with a score higher than the first threshold or lower than the second threshold, e.g. they may not be given the drug but may be monitored more closely to detect onset of the disease should it occur. The treatment of individuals with the intermediate risk may rely more heavily on other information, such as clinical information about the disease, polygenic test, drug, patient, etc., than does the treatment of individuals who do not have an intermediate risk (i.e. are at "high" or "low" risk).

Although a set of associated loci may be identified by an association study, not all of the associated loci need be used in a single polygenic test. Once a set of associated loci is identified, one may adjust the number of associated loci to be used in a polygenic test and analyze the value of the test, e.g., with regards to its sensitivity, specificity, relative risk, likelihood ratio, PPV, NPV, accuracy, or a combination thereof. For example, in certain embodiments, a high relative risk in combination with a high sensitivity is preferred. In one aspect, the methods of the present invention may be used to determine a subset (e.g., at least about 5, 10, 15, 20, 30 or 50) of associated loci to be used in a polygenic test. For example, the associated loci with the greatest allele frequency differences between the case group and the control group may be selected. In some embodiments, only those loci with allele frequency differences of at least about 8% (0.08), 10% (0.1), 15% (0.15), or 25% (0.25) are chosen for use in a polygenic test. In some embodiments, the subset of associated loci to be used in a polygenic test is determined by analyzing certain characteristics of the resultant polygenic test using the genotyping data from the case and control groups. For example, sensitivity, specificity, relative risk, likelihood ratio, PPV, NPV, accuracy, or a combination thereof may be determined for a hypothetical polygenic test using a given subset of associated loci. A plurality of such hypothetical polygenic tests may be analyzed in this manner and the subset of associated loci that in combination result in the polygenic test with the best combination of these characteristics may be chosen. As in determining an appropriate threshold value as discussed above, the best combination of sensitivity, specificity, relative risk, likelihood ratio, PPV, NPV, accuracy or a subset thereof for a polygenic test is dependent on many clinical factors including, e.g., the severity of the phenotype, the prevalence of the phenotype, and other clinical information that is population-specific or patient-specific. In certain embodiments, subset of associated loci to be used in a polygenic test is determined based on a combination of the allele frequency differences for the associated loci and the characteristics of the resulting polygenic test. Thus, using the methods of the present invention, one may predict the characteristics of a polygenic test using a subset of associated loci without performing a case-control study using only that subset to measure such characteristics.

This aspect of the present invention has important practical implications. For example, if certain associated loci do not replicate in a second validating association study, they may be removed from the set of associated loci to be used in a polygenic test, and the characteristics of the polygenic test without the "nonreplicating" loci may be determined without performing another association study. Further, a polygenic test that requires a large number of loci to be genotyped is more expensive to perform than a polygenic test that requires a small number of loci to be genotyped. Thus, the ability to reduce the number of associated loci in a polygenic test while maintaining specific desired characteristics (e.g., sensitivity, relative risk, etc.) for has direct implications for the affordability of performing such a test, and therefore on the practical applicability of such a test.

Identification of Individuals at Risk of Developing a Multifactorial Disease

Once one or more threshold values have been determined, an individual ("test individual") who is not a member of the case or control groups may be examined to determine the risk that the individual will develop or exhibit the trait of interest. In certain embodiments of the present invention, the test individual is of the same species as the individuals in the case and control groups. The test individual is genotyped at each of the associated SNP loci. A score is calculated for the test individual based on their genotype at each of the SNP loci in the same manner as scores were calculated for the individuals in the original case and control groups. In one embodiment of the present invention, the calculated score for the test individual is compared to one or more threshold values to determine whether or not that individual is likely to exhibit the disease. For example, if a test individual has a score greater than a first threshold value, it may be considered likely the test individual will develop or exhibit the disease, and if the test individual's score is equal to or less than a second threshold value, the test individual may be considered to be at low risk of developing the disease. The first and second threshold values may be the same or different values. For example, in an embodiment in which 55 is chosen as both the first and second threshold, then a test individual having a score greater than 55 may be diagnosed as likely to develop the disease, and a test individual having a score of 55 or less may be diagnosed as unlikely to develop the disease. Further, based on the prevalence of the disease and the sensitivity and specificity of the genetic test, one may calculate the probability or likelihood that a person who is identified as at high risk by the test actually has or will develop the disease (e.g. post-test odds, as discussed above). Likewise, one may calculate the probability or likelihood that a person who is identified as at low risk by the test actually does not have and will not develop the disease.

In another embodiment of the present invention, a relative risk is computed for a test individual to further analyze the likelihood that the individual will develop or exhibit the disease. Relative risk is a measure of how much a particular risk factor influences the risk of a specified outcome. For example, a relative risk of 2 associated with a risk factor means that persons with that risk factor have a two-fold increased risk of having a specified outcome than persons without that risk factor. In one aspect, a relative risk for a disease is a fold-increase in risk relative to the risk of the trait (e.g. disease) in the general population. A relative risk is determined by calculating the ratio of the percentage of individuals in the case group to the percentage of individuals in the control group that meet or exceed a given score based on their genotypes at the set of SNPs that are associated with the disease. Using the data presented in Table 1, for example, the relative risk of an individual with a score of at least 65 is (0.64)/(0.02)=32, which means that the individual has a 32-fold increased risk of developing the disease based on their allelic composition at the associated SNP positions. To compare, the relative risk of an individual with a score of at least 70 is (0.5)/(0.005)=100, which means that the individual has a 100-fold increased risk of developing the disease based on their allelic composition at the associated SNP positions. In one aspect of the present invention, a score is calculated for a test individual based on their genotypes at the associated SNP loci, and the case and control groups are analyzed to determine what percentage of the case individuals and what percentage of the control individuals have a score that is at least as great as that of the test individual. Next, the percentage of case individuals with a score at least as great as that of the test individual is divided by the percentage of control individuals with a score at least as great as that of the test individual to compute the relative risk for the test individual.

As noted above, the relative risk provides a fold-increase in risk relative to the risk of the disease in the general population. Therefore, to determine the test individual's risk of developing the disease, the relative risk for the individual must be combined with clinical information regarding the prevalence of the disease. For example, if the disease has a prevalence of 1:100, then an individual with a relative risk of 32 has a probability of developing the disease of 32:100, or 0.32. However, for a disease that has a prevalence of 1:1,000,000, an individual with a relative risk of 32 has a probability of developing the disease of 32:1,000,000, or 0.000032. Thus, although the relative risks were the same in these two examples, the actual probability of developing the disease was very different for these two diseases. In certain aspects of the present invention, a test individual's risk of developing a multifactorial trait of interest is calculated by multiplying the relative risk determined for the individual by the prevalence of the multifactorial trait in the general population. Determination of relative risk is widely known and routinely performed by those of skill in the art (see Sackett, et al. (1991) *Clinical Epidemiology: a basic science for clinical medicine* (second edition) Little Brown, Boston).

Further, the PPV and NPV of a genetic test can provide information regarding the risk that an individual has or will develop a disease based on the test result. For example, if an individual tests "positive" for the disease using a test with a PPV of 0.87 and an NPV of 0.99, then the individual has an 87% chance of having or developing the disease. Likewise, if another individual tests "negative" for the disease using the same test, then that individual has only a 1% chance of having or developing the disease.

Likelihood ratios use the sensitivity and specificity of a test to provide a measure of how much a particular test result changes the likelihood that a patient has or does not have a multifactorial trait of interest, as discussed above. The likelihood ratio (LR) of a positive test result (LR+) is calculated as the sensitivity divided by (1−specificity), and the LR of a negative test result (LR−) is calculated as (1−sensitivity) divided by the specificity. These LR values are multiplied by the pre-test odds to compute the post-test odds, which represents the chances that the individual has or will develop the multifactorial trait by incorporating information about the disease prevalence, the patient pool, and specific patient risk factors (pre-test odds) and information about the diagnostic test itself (LR). The post-test odds may be used to compute the post-test probability by dividing the post-test odds by (1+post-test odds). For example, if an individual who tests positive has a pre-test odds of one to 66 based on a prevalence of 1.5%, and the test has an LR+ of 6.6, then the post-test odds will be 0.1 and the post-test probability will be 0.09, meaning that the individual has a 9% chance of having the disease. Similarly, if an individual who tests negative has a pre-test odds of one to three and the test has an LR− of 0.09, then the post-test odds will be 0.03, corresponding to a post-test probability of 3% that the individual has the disease. In this way, likelihood ratios and prevalence of the multifactorial trait may be used to calculate a probability that an individual has or will develop a multifactorial trait of interest based on a given test result.

Prognostic and Diagnostic Uses

Preventative measures are successful in preventing many different diseases, but these measures are only successful if individuals can be identified as at risk of developing the disease before onset of the disease. The onset of multifactorial diseases is especially difficult to predict due to the complex set of factors that influence their development. As such, individuals often do not know they are at risk of developing a multifactorial disease until it is too late to prevent it. It will be clear to one of skill in the art that the methods presented may serve as valuable tools for clinicians in making medical decisions regarding the care of their patients. The determination of risk is an important aspect of the clinical analysis of an individual used to determine whether or not medical interventions are warranted, and which interventions are most appropriate for a given individual (Bucher, et al. (1994) *BMJ* 309(6957):761–764; Forrow, et al. (1992) *Am J Med* 92(2)121–124).

In certain embodiments, the present invention provides methods for identifying individuals at risk of developing a disease (prognostics), thereby allowing implementation of measures to prevent or delay the onset of the disease. In one embodiment, an individual's risk of developing a given disease may be determined by comparing a score based on the individual's genotype at a set of disease-associated SNPs to at least one threshold value. If the individual's score exceeds a threshold value, the institution of preventative measures (e.g., radiation or drug therapies) may be justified. In another embodiment, an individual's risk of developing a disease may be determined by calculating a relative risk for the individual and multiplying the relative risk by the prevalence of the disease. In another embodiment, the sensitivity, specificity, PPV, NPV, and/or accuracy of a genetic test is used to calculate an individual's risk of developing the disease. In yet another embodiment, the LR for the test is used to calculate the post-test odds/probability that the individual will develop the disease. In another embodiment, a combination of the above-described methods are used to determine an individual's risk of having or developing the disease. This information may be used by a clinician to better determine an appropriate treatment regimen for the individual. Often, this information is used in combination with clinical information regarding the disease, the patient, or the population from which the patient comes.

In some aspects, the methods presented herein may also be used to identify individuals who are resistant to a disease. For example, some individuals who have a family history of a disease (e.g., breast cancer) never develop the disease. This knowledge could better assess the risk of these individuals of developing the disease in question, provide peace of mind to those who are not at high risk, and in some cases would preclude drastic prophylactic treatments (e.g., elective mastectomy). The methods presented herein may also be used to identify individuals with an increased risk of developing an adverse, non-disease condition and thereby motivate lifestyle changes to prevent onset of the condition. For example, a polygenic test comprising set of SNPs associated with hypertension could provide strong incentive to those who are found to be at high risk to exercise and eat a healthy diet.

Some diseases are difficult to diagnose based solely on the physical symptoms apparent in a patient. The diagnosis of these diseases is often confounded by the variety of ways such a disease may manifest itself in different individuals, and/or the fact that its symptoms may be similar to those of a number of unrelated diseases. In a further aspect of the present invention, a set of SNPs associated with such a disease may be used to aid in the diagnosis of an individual who exhibits a phenotype that may be indicative of the disease. Thus, genotyping the individual for the set of associated SNPs and determining the individual's risk of exhibiting the disease could either support or argue against the diagnosis suggested by the physical symptoms. If the diagnosis was supported, a clinician could use this information to make treatment decisions for the individual, such as initiating a treatment regimen for the disease. For example, celiac disease is an autoimmune disorder of the digestive system that damages the small intestine and interferes with the absorption of nutrients from food. Specifically, celiac disease causes an inflammatory response in the small intestine in response to gluten, a protein found in wheat, rye, and barley, and the only treatment for celiac disease is a gluten-free diet. It is difficult to diagnose celiac disease because different individuals display different symptoms. For example, some will have primarily gastrointestinal symptoms such as distended abdomen or diarrhea, while others will have only irritability or depression. Further, the condition can be easily misdiagnosed because its symptoms are similar to many other conditions including irritable bowel syndrome, Crohn's disease, ulcerative colitis, diverticulosis, intestinal infections, chronic fatigue syndrome, and depression. The methods presented herein may be used to identify a set of genetic loci associated with celiac disease, and these loci may be used to screen individuals who display symptoms indicative of celiac disease. Those individuals who are found to be at high risk of developing celiac disease based on their genetic composition may be diagnosed as having celiac disease and placed on a gluten-free diet.

In other embodiments, the methods presented herein may be used to aid in the determination of whether or not a prophylactic therapy is warranted to prevent development of e.g. a disease in an individual. For example, there are approved therapeutics for prevention of breast cancer that are dependent on historical clinical information such as family history, onset of first menstrual period, number of children, etc. These factors, although useful for computing a pre-test odds, are only marginally predictive of whether or not a woman will develop breast cancer. A genetic test to be used in combination with the pre-test odds would provide a far superior means of deciding whether or not to treat an individual prophylactically (e.g. with tamoxifen) by providing a much more accurate way to identify and quantify her risk of developing breast cancer.

In one aspect of the present invention, a prognostic or diagnostic assay is provided comprising a nucleic acid array that contains probes designed to detect the presence of the set of associated SNPs in a biological sample. Nucleic acids are isolated from a biological sample from a test individual and are hybridized to the probes on the nucleic acid array. The probe intensities are analyzed to provide a genotype for the test individual at each of the associated SNP positions. The genotypes are used to compute a score for the test individual, and the individual's risk of developing the disease is determined according to the methods presented herein.

The set of associated SNPs may further be used for identifying regions of the genome that are involved in development of the disease phenotype. These SNPs may be directly involved in the manifestation of the disease, or they may be in linkage disequilibrium with loci that are directly involved. For example, a disease-associated SNP may affect the expression or function of a disease-associated protein directly, or may be in linkage disequilibrium with another locus that affects the expression or function of the protein. Examples of direct effects to the expression or function of a protein include, but are not limited to, a polymorphism that alters the polypeptide sequence of the protein, and a polymorphism that occurs in a regulatory region (i.e., promoter, enhancer, etc.) resulting in the increased or decreased expression of the protein. In certain embodiments, genomic regions containing the set of associated SNPs are analyzed to identify genes that are directly involved in the biological basis of the disease ("identified genes").

The associated SNPs that lie in the coding region of a gene may be used to detect or quantify expression of an associated allele in a biological specimen for use as a diagnostic marker for the disease. For example, nucleic acids containing the associated SNPs may be used as oligonucleotide probes to monitor RNA or mRNA levels within the organism to be tested or a part thereof, such as a specific tissue or organ, so as to determine if the gene encoding the RNA or mRNA contains an associated allele. In one aspect, a diagnostic or prognostic kit is provided that comprises oligonucleotide probes for use in detecting an associated allele in a biological sample. Likewise, if the associated allele causes a change in the polypeptide sequence of the encoded protein, the allelic constitution of the gene may be assayed at the protein level using any customary technique such as immunological methods (e.g., Western blots, radio-immune precipitation and the like) or activity based assays measuring an activity associated with the gene product. In one aspect, a diagnostic or prognostic kit is provided that comprises an assay for detecting a polypeptide encoded by an associated allele in a biological sample. The manner in which cells are probed for the presence of particular nucleotide or polypeptide sequences is well established in the literature and does not require further elaboration here, however, see, e.g., Sambrook, et al., *Molecular Cloning: A Laboratory Manual* (Cold Spring Harbor Laboratory, New York) (2001).

Therapeutics

The set of associated SNPs may be useful for developing therapeutics for the prevention of disease. In one aspect, the identified genes may be used for gene therapy. For example, if an identified gene is found to be downregulated in individuals who exhibit the disease, then upregulation of the gene could be an effective strategy to prevent onset of the disease in test individuals. Upregulation of the identified gene may be accomplished by incorporating an allele of the gene that is not associated with the disease into an expression vector and further introducing the vector into an organism, thereby upregulating the expression of the gene in the organism. Such vectors generally have convenient restriction sites located near the promoter sequence to provide for the insertion of nucleic acid sequences in a recipient genome. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced directly into tissues or host cells by any number of routes, including viral infection, microinjection, or fusion of vesicles. Jet injection may also be used for intramuscular administration, as described by Furth, et al., *Anal. Biochem*, 205: 365–68 (1992). Alternatively, the DNA may be coated onto gold microparticles, and delivered intradermally by a particle bombardment device or "gene gun" as described in the literature (see, for example, Tang, et al., *Nature*, 356: 152–54 (1992)).

Proteins encoded by the identified genes may be targets for antibody therapy if there is an amino acid change in the sequence of the protein that is associated with the a predisposition to the disease. For example, if an associated allele encodes a protein variant that is a causative factor for the disease, antibodies specific for the disease-associated protein variant may be administered to a patient as a means to inhibit the development of the disease. In certain embodiments, a combination of antibodies, each specific for a different disease-associated protein, may be administered to a patient to prevent onset of a disease.

Antisense molecules may be used to down-regulate expression of an associated allele of an identified gene in cells. An antisense molecule forms a duplex with the mRNA encoded by an allele of a gene, thereby down-regulating its expression and blocking translation of the corresponding protein. For example, an antisense reagent may be developed based on the sequence of the mRNA encoded by an associated allele. This antisense agent may then be administered to a heterozygous patient (possesses one associated allele and one allele that is not associated with the disease) to decrease the expression of the associated allele, allowing the expression of the unassociated allele to predominate. The antisense reagent may be antisense oligonucleotides, particularly synthetic antisense oligonucleotides having chemical modifications, or nucleic acid constructs that express such antisense molecules as RNA. A combination of antisense molecules may be administered, where a combination may comprise multiple different sequences.

As an alternative to antisense inhibitors, catalytic nucleic acid compounds, e.g., ribozymes, anti-sense conjugates, etc., may be used to inhibit expression of associated alleles. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res.* 23: 4434–42 (1995)). Examples of oligonucleotides with catalytic activity are described in WO 9506764. Conjugates of antisense oligonucleotides with a metal complex, e.g. terpyridylCu(II), capable of mediating MRNA hydrolysis are described in Bashkin, et al., *Appl. Biochem. Biotechnol.* 54: 43–56 (1995).

An expressed protein encoded by an identified gene may be used in drug screening assays to identify ligands or substrates that bind to, modulate or mimic the action of that protein product, and thereby identify therapeutic agents to provide, for example, a replacement or enhancement for protein function in affected cells, or an agent that modulates or negates protein function. A wide variety of assays may be used for this purpose, including labeled in vitro protein-protein binding assays, protein-DNA binding assays, electrophoretic mobility shift assays, immunoassays for protein binding, and the like. The term "agent" as used herein describes any molecule, e.g., a protein or small molecule, with the capability of altering, mimicking or masking, either directly or indirectly, the physiological function of an identified gene or gene product. Generally pluralities of assays are run in parallel with different concentrations of the agent to obtain a differential response to the various concentrations. Typically, one of these concentrations serves as a negative control, e.g., at zero concentration or below the level of detection. Also, all or a fragment of a purified protein variant may be used for determination of three-dimensional crystal structure, which can be used for determining the biological function of the protein or a part thereof, modeling intermolecular interactions, membrane fusion, etc.

Candidate agents encompass numerous chemical classes, though typically they are organic molecules or complexes, preferably small organic compounds, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be coupled to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures. A variety of other reagents may be included in the screening assay. These include reagents like salts, neutral proteins, e.g., albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc., may be used.

Agents may be combined with a pharmaceutically acceptable carrier or diluent, including any and all solvents, dispersion media, coatings, anti-oxidant, isotonic and absorption delaying agents and the like. The agent may be combined with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with buffering agents, moistening agents, preservatives and flavoring agents. The use of such media and agents for pharmaceutically active substances is well known in the art and are readily available to the public. Moreover, pharmaceutically acceptable auxiliary substances, such as pH adjusting and buffering agents, tonicity adjusting agents, stabilizers, wetting agents and the like, are readily available to the public. Except insofar as any conventional media or agent is incompatible with the active ingredient, its use in the therapeutic compositions and methods described herein is contemplated. Supplementary active ingredients can also be incorporated into the compositions.

The following methods and excipients are merely exemplary and are in no way limiting. Identified agents of the invention can be incorporated into a variety of formulations for therapeutic administration. More particularly, the complexes can be formulated into pharmaceutical compositions by combination with appropriate, pharmaceutically acceptable carriers or diluents as discussed supra, and may be formulated into preparations in solid, semi-solid, liquid or gaseous forms, such as tablets, capsules, powders, granules, ointments, solutions, gels, microspheres, and aerosols. Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The agents identified by the methods presented herein can be formulated into pressurized acceptable propellants such as dichlorodifluoromethane, propane, nitrogen and the like. Alternatively, agents may be made into suppositories for rectal administration by mixing with a variety of bases such as emulsifying bases or water-soluble bases and can include vehicles such as cocoa butter, carbowaxes and polyethylene glycols, which melt at body temperature, yet are solid at room temperature.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well-tolerated by the host. The implant containing identified agents may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms depend on the particular compound employed and the effect to be achieved, and the pharmacodynamics associated with each active agent in the host.

Administration of the agents can be achieved in various ways. The formulation may be given orally, by inhalation, or may be injected, e.g. intravascular, intratumor, subcutaneous, intraperitoneal, intramuscular, etc. Agents may be topical, systemic, or may be localized by the use of an implant that acts to retain the active dose at the site of implantation. The dosage of the therapeutic formulation will vary, depending on the specific agent and formulation utilized, the nature of the disease, the frequency of administration, the manner of administration, the clearance of the agent from the host, and the like, such that it is sufficient to address the disease or symptoms thereof, while minimizing side effects. In some cases, oral administration will require a different dose than if administered intravenously. The compounds will be administered at an effective dosage such that over a suitable period of time the disease progression may be substantially arrested. The initial dose may be larger, followed by smaller maintenance doses. The dose may be administered as infrequently as once, weekly or biweekly, or fractionated into smaller doses and administered daily, semi-weekly, etc., to maintain an effective dosage level. Treatment may be for short periods of time, e.g., after ventricular fibrillation, or for extended periods of time, e.g., in the prevention of further episodes of ventricular fibrillation. It is contemplated that the composition will be obtained and used under the guidance of a physician for in vivo use.

Pharmacogenomics

In other embodiments, the set of associated SNPs identified by the methods of the present invention are used for pharmacogenomics and drug development. Due to the great number of treatment options available for common multifactorial diseases, it is often difficult to determine which of a group of treatment options will be most effective for a given patient. Typically, several different options must be tried before one is found that is safe and effective. In the meantime, the patient will continue to suffer the effects of the disease, and perhaps will also experience adverse events in response to one or more of the treatment options tested. The methods presented herein are useful for stratifying patient populations prior to initiation of a treatment regimen. Polymorphic loci are identified that are associated with the response of a patient to a drug or other medical treatment. The response may be an adverse event or may be related to the efficacy of the treatment. The associated loci are used to screen patient populations to generate genetic profiles relating to the associated loci for the patients that will help clinicians determine which individuals should be given the drug or medical treatment and which should not. For example, individuals who are predisposed to exhibiting an adverse event and individuals who are unlikely to have an efficacious response to a drug may be excluded from treatment with that drug, and may instead be treated by alternate means (different drug or other medical treatment).

In one such embodiment, individuals are screened for a set of SNPs that are associated with a disease that confers a known risk of an adverse response to a particular drug treatment. Those individuals at high risk of developing the disease are excluded from the treatment regimen. For example, individuals with LQTS (long QT syndrome) have a high risk of ventricular fibrillation when administered antiarrhythmia drugs. It would be beneficial to screen a patient population for a set of loci associated with LQTS prior to administering such a drug, and to exclude those individuals at high risk of developing LQTS. The set of SNPs associated with the disease is determined by performing an association study, and an individual's risk of developing the disease is performed as described above. A high risk of developing the disease may be considered a risk factor for adverse events in response to an antiarrhythmia drug and this information may be used by a clinician to determine appropriate treatment options for the individual. For example, if the individual has a high risk of developing the disease, then administration of the drug may be avoided. If the individual has a low risk of developing the disease, then administration of the drug may be a viable treatment option.

In another embodiment of the present invention, the effectiveness of a drug treatment regimen is predicted for an individual based on the genotypes of the individual at a set of SNPs associated with efficacy of the drug. This information is used to determine a probability of whether the drug will be an effective treatment for the individual, or if other drugs or treatment options should be considered instead. For example, an association study may be performed using a case group of individuals that do not have an efficacious response to the drug ("nonresponders") and a control group of individuals that have an efficacious response ("responders"). Members of the case and control groups are genotyped at a plurality of SNP positions, relative allele frequencies are computed for each of the SNPs, and a set of SNPs associated with an efficacious response is identified as those SNPs that have allele frequency differences that are significantly different between the case and control groups. A score is calculated for each member of the case and control groups based on their genotypes at the associated SNPs, and these scores are used to determine one or more appropriate threshold values for a genetic test that will predict the risk of an individual not having an efficacious response to the drug. The determination of an appropriate threshold value may also include one or more of the following: clinical knowledge of the drug, the indication being treated, and the patient population, and calculation of sensitivity, specificity, PPV, NPV, accuracy, LR+ and LR− of the genetic test. An individual who is a candidate for receiving the drug is genotyped at each of the associated SNP positions, and a score is calculated for the individual based on his/her genotypes at the set of associated SNPs. If the individual has a score that is greater than a threshold value, the individual may be classified as likely to be a nonresponder, and alternative treatments may be considered. If the individual has a score equal to or less than a threshold value, the individual may be classified as likely to be a responder and administration of the drug may be recommended. In another embodiment, an individual's risk of being a nonresponder may be determined by calculating a relative risk for the individual and multiplying the relative risk by the prevalence of nonresponders based on the known efficacy of the drug. In another embodiment, the individual's likelihood of being a responder is computed using the accuracy, LR+, LR−, PPV and/or NPV of the polygenic test. This information can then be used by a clinician in deciding on appropriate treatments for the individual.

In a related embodiment, a diagnostic may be developed for a therapeutic area to enable a clinician to better individualize treatment of patients. Rather than focusing on a single drug, the therapeutic area diagnostic would provide information on the likelihood that a patient will be a responder for a series of drugs related to a single therapeutic area. For example, there are a multitude of drugs on the market for treating depression including SSRIs (selective serotonin reuptake inhibitors), TCAs (tricyclic antidepressants), MAOIs (monoamine oxidase inhibitors), and triazolopyridines. Association studies may be performed to identify polymorphic loci associated with the efficacy of each of these types of drugs, and those loci could then be used to screen patient populations to determine which class of drugs would be most efficacious for a given individual. For each drug, a case group comprises individuals with depression that had an efficacious response to the drug, and a control group comprises individuals that did not have an efficacious response to the drug. Associated SNPs are identified as those that have a significantly different allele frequency in the cases than in the controls. For each class of drug, thresholds are determined that will identify individuals with a high (e.g. >80%, or >90% or >95%, or >98%) chance of having an efficacious response. An individual in need of antidepressant therapy is screened for the SNPs that are associated with each of the drug types, and a clinician determines an appropriate therapy choice for the individual based on the individual's genotype information and the thresholds determined for each class of drug.

In a further related embodiment, SNPs associated with the efficacy of a drug may be used to improve the efficacy of the drug by stratifying patient populations to exclude probable nonresponders from treatment. In one example, ~32% of patients exposed to a drug are classified as responders. An association study is performed with a case group of responders and a control group of nonresponders, and 25 SNPs are found to be associated with the responder phenotype. Based on the scores calculated for the cases and controls it is found that 81% of responders and 40% of nonresponders have a score of >19. Therefore, using 19 as a threshold value to stratify a patient population prior to administering the drug improves the overall efficacy of the drug from ~32% to ~50%. In doing so, the number of nonresponders exposed to the drug is decreased substantially, and those excluded may then be treated with alternative therapies sooner. A change in efficacy of this magnitude could help to get a new drug approved, or could encourage wider use of an already approved drug.

In yet another embodiment, the methods presented herein may be used to assess whether a brand name drug should be used, or if a cheaper generic may be substituted instead. For example, an association study would be performed to identify genetic loci associated with a positive clinical response to the generic alternative. Patients in need of treatment would then be genotyped at these associated loci and a score would be calculated. The individual's score would then be used to predict the efficacy of the generic drug in the individual, and a clinician would use this information to make a treatment decision for the individual. This application of the disclosed methods could be used for medical costs reimbursement decisions, as well. For example, if it was found that the generic drug was unlikely to be efficacious in individual A, then the brand name drug would be administered to A and the cost of the brand name drug could be reimbursed to A; however, if individual B was likely to have an efficacious response to the generic, then individual B would not be given the more expensive brand name drug, and only the cost of the generic would be reimbursable.

In another embodiment of the present invention, the risk that an individual will experience an adverse event in response to administration of a drug is determined based on the genotypes of the individual at a set of SNPs associated with the occurrence of adverse events related to the drug. If an individual is found to have a high risk of experiencing an adverse event in response to a treatment regimen, then the treatment regimen may be avoided and other treatment options may be considered. For example, an association study may be performed using a case group of individuals that exhibited an adverse event in response to the drug and a control group of individuals that did not exhibit the adverse event. Members of the case and control groups are genotyped at a plurality of SNP positions, relative allele frequencies are computed for each of the SNPs, and SNPs associated with the adverse event are identified as those SNPs that have allele frequency differences that are significantly different between the case and control groups. A score is calculated for each member of the case and control groups based on their genotypes at the associated SNPs, and these scores are used to determine one or more appropriate threshold values for a polygenic test that will predict the risk that an individual will experience an adverse event in response to the drug with appropriate levels of sensitivity, specificity, PPV, NPV, LR+, LR− and/or accuracy. As discussed above, the selection of a threshold value may also be based on clinical factors, such as the severity of the adverse event, the disease or disorder being treated, and the medical history of the individual being treated. For example, if the adverse event is death, then a high sensitivity is essential to identify those individuals who have a high probability of dying if administered the drug. Prior to receiving the drug, an individual is genotyped at each of the associated SNP positions, and a score is calculated for the individual based on his/her genotypes at the set of associated SNPs. For example, if the individual has a score that is greater than a threshold value determined from the scores of the case and control groups, the individual may be classified as likely to experience an adverse event if administered the drug, and use of the drug may be avoided. If the individual has a score equal to or less than a threshold value, the individual may be classified as not likely to suffer an adverse event and administration of the drug may be recommended. If the individual has a score less than or equal to one threshold value and greater than another threshold value, the individual may be classified as having an intermediate likelihood of experiencing an adverse event and alternative drug therapies may be used, or the drug may be administered e.g. only with close monitoring, or in combination with another therapeutic to counteract the adverse event. Determination of the best treatment regimen for an individual with an intermediate risk of experiencing an adverse event may rely more heavily on other information (e.g. clinical data, FDA or patient input, etc.) than does determination of the best treatment regimen for an individual with a very high or low risk. In another embodiment, an individual's risk of experiencing an adverse event may be determined by calculating a relative risk for the individual and multiplying the relative risk by the known prevalence of individuals experiencing adverse events. This information can then be used by a clinician in deciding on appropriate treatments for the individual. Adverse events in response to administration of a drug include, but are not limited to, allergic reactions, cardiac arrhythmia, stroke, bronchospasm, gastrointestinal disturbances, fainting, impotency, rashes, fever, muscle pain, headaches, nausea, birth defects, hot flashes, mood changes, dizziness, agitation, vomiting, sleep disturbance, somnolence, insomnia, addiction to the drug, and death.

In a related embodiment, SNPs associated with the safety of a drug may be used to improve the safety of the drug by stratifying patient populations to exclude from treatment those individuals likely to exhibit an adverse event in response to administration of the drug. In one example, a new drug is found to have excellent efficacy, tolerance and convenience, however 4% of individuals treated with the drug experience a severe adverse event, and this incidence of adverse events has limited the use of the drug, e.g. to only those individuals for whom other therapies have failed. However, a regulatory agency has stipulated that if the incidence of the adverse event were lowered by at least 50% then the drug could be approved for wider usage. This could be achieved if individuals who are likely to experience the adverse event could be identified prior to treatment, so an association study is performed with a case group of individuals that experienced the adverse event and a control group of individuals that did not to identify a set of 20 SNPs associated with the adverse event. Results from the association study are presented in Table 3 with the risk cutoff values shown in the first column, the % of cases with scores greater than the corresponding risk cutoff value in the second column, the % of controls with scores greater than the corresponding risk cutoff value in the third column, the relative risk in the fourth column, the percent sensitivity in the fifth column, the percent specificity in the sixth column, the PPV (as a percent) in the seventh column, and the NPV (as a percent) in the eighth column.

TABLE 3

| Risk Cutoff Value | % Cases | % Controls | Relative risk | Sensitivity | Specificity | PPV | NPV |
|---|---|---|---|---|---|---|---|
| 20 | 40.0% | 2.8% | 14.2 | 40.0% | 97.2% | 37.3% | 97.5% |
| 19 | 51.6% | 5.6% | 9.2 | 51.6% | 94.4% | 27.7% | 97.9% |
| 18 | 58.0% | 9.9% | 5.4 | 58.0% | 90.1% | 19.6% | 98.1% |
| 16 | 75.0% | 28.5% | 2.5 | 75.0% | 71.5% | 9.9% | 98.6% |
| 15 | 91.2% | 39.8% | 2.3 | 91.2% | 60.2% | 8.7% | 99.4% |

Using these values, it is found that using 19 as a threshold value would eliminate approximately 51.6% of the patients at highest risk for the adverse event while only eliminating 5.6% of those who could benefit from the drug. Therefore, if 1000 subjects were screened using 19 as the threshold value and assuming that 4% of them are at high risk of experiencing the adverse event, 74 [(1000)(0.04)(0.516)+(1000)(0.96)(0.056)] would be excluded and the remaining 926 could be treated. The risk of adverse events to those treated would therefore be [(10000)(0.04)(1−0.516)/926=0.02], or 2%. Thus, using 19 as a threshold value in a diagnostic to stratify patient populations prior to administering the drug would reduce the incidence of adverse events from 4% to 2%, thereby qualifying the drug for wider usage. Similarly, the 18 could also be used as a threshold value, which would exclude 23/1000 individuals and would result in an expected incidence of adverse events in the treated individuals of 1.9%. However, this decrease in incidence of adverse events is coupled with a decrease in both the specificity and the PPV for the test. The selection of an appropriate risk/benefit diagnostic threshold value may require not only information about the test itself (specificity, sensitivity, PPV, NPV, etc.), but also interaction between the practitioner of the methods presented herein an a regulatory agency (e.g. FDA) and judgment based on clinical utility. The goal of such a pharmacogenomics test would be to maximize the NPV (reduce the incidence of the adverse event in those treated) while balancing the PPV (minimizing the exclusion of patients who could benefit from the drug). The use of the methods described herein to reduce the frequency of adverse events could help to get a new drug approved, or could encourage the wider use of an already approved drug. For example, by coupling such a diagnostic to a drug it may be possible to reduce the frequency of adverse events to levels that are commercially acceptable, in effect rescuing a drug that would otherwise not have been approved.

It will be clear to those of skill in the art that an appropriate threshold value for approval of a diagnostic to be coupled to a drug is largely dependent on negotiations between a drug sponsor (e.g. a pharmaceutical company) and the regulatory authorities (e.g. F.D.A.). This is the case whether the diagnostic is for improving the efficacy or safety of a drug. For example, although the frequency of adverse events is lowered to 2% in the example above, the regulatory authorities may require a more stringent safety level, and therefore a lower threshold value to identify individuals to exclude from treatment with the drug, thereby sacrificing PPV for a higher NPV.

In certain aspects, the present invention provides greatly improved methods for determining an individual's risk of developing or exhibiting a multifactorial trait. In certain aspects, the methods are further used to develop prognostics, diagnostics, or therapeutics for a multifactorial disease. In other aspects, the methods are further used to predict drug response in individuals prior to administration of a therapeutic regimen. The methods presented herein may further help to reduce the overall cost of medical treatment by providing a means to quickly find the right medical intervention (most efficacious, safest, cheapest, etc.) for an individual so that precious time and money are not misspent on therapies of limited value. It is to be understood that the above description is intended to be illustrative and not restrictive. It readily should be apparent to one skilled in the art that various embodiments and-modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method for assessing an individual's likelihood of developing or exhibiting a multifactorial trait comprising
    a) determining a genotype for said individual at a plurality of biallelic polymorphic loci, wherein each of said plurality has an associated allele and an unassociated allele, and further wherein the genotype is selected from the group consisting of homozygous for the associated allele, heterozygous, and homozygous for the unassociated allele;
    b) computing a score for said individual based on said genotype determined in a); and
    c) performing a comparison of the score to at least one threshold value, wherein said comparison is used to assess said individual's likelihood of developing or exhibiting said multifactorial trait and to further determine an appropriate course of treatment for said individual.

2. The method of claim 1, further comprising identifying the associated alleles and the unassociated alleles for said plurality of biallelic polymorphic loci by performing an association study with a case group that exhibits the multifactorial trait and a control group that does not exhibit the multifactorial trait, thereby determining a set of alleles of said polymorphic loci that are significantly more abundant in the case group than the control group, wherein said set of alleles or a subset thereof are the associated alleles.

3. The method of claim 2, wherein the case group and the control group each comprise at least 50 individuals.

4. The method of claim 2, wherein at least one of said case and said control group comprises at least 100 individuals.

5. The method of claim 2, wherein at least one of said case and said control group comprises at least 200 individuals.

6. The method of claim 2, wherein at least one of said case and said control group comprises at least 500 individuals.

7. The method of claim 2, wherein said case and control group comprise individuals that are mammals, reptiles, amphibians, fish, birds, crustaceans, insects, plants, bacteria, viruses, or archaeans.

8. The method of claim 2, wherein said case and control group comprise individuals that are humans.

9. The method of claim 2, wherein said case and said control groups are matched prior to performing the association study.

10. The method of claim 2, wherein said performing an association study further comprises
    a) genotyping said case group and said control group at a set of polymorphic loci that comprises said plurality of biallelic polymorphic loci;
    b) calculating a relative allele frequency for each of said set of polymorphic loci for each of said case group and said control group;
    c) for each of said set of polymorphic loci, comparing the relative allele frequency calculated for the case group with the relative allele frequency calculated for the control group, thereby identifying a subset of said set of polymorphic loci, wherein each of said subset has a relative allele frequency that is significantly different for the case group than for the control group; and
    d) determining an allele for each of said subset that is more abundant in said case group than said control group, wherein said allele is one of said associated alleles.

11. The method of claim 10, wherein the set of polymorphic loci comprises at least about 500 polymorphic loci.

12. The method of claim 10, wherein the set of polymorphic loci comprises at least about 1000 polymorphic loci.

13. The method of claim 10, wherein the set of polymorphic loci comprises at least about 10,000 polymorphic loci.

14. The method of claim 10, wherein the set of polymorphic loci comprises at least about 100,000 polymorphic loci.

15. The method of claim 10, wherein the set of polymorphic loci comprises at least about 1,000,000 polymorphic loci.

16. The method of claim 10, wherein the set of polymorphic loci comprises polymorphic loci from one or more chromosomes in the genome of said individual.

17. The method of claim 10, wherein the set of polymorphic loci comprises polymorphic loci from every chromosome in the genome of said individual.

18. The method of claim 10, wherein the set of polymorphic loci comprises multiple polymorphic loci from every chromosome in the genome of said individual.

19. The method of claim 2, wherein said association study is performed using an individual genotyping methodology.

20. The method of claim 2, wherein said association study is performed using a pooled genotyping methodology.

21. The method of claim 20, further comprising validating said associated alleles by performing a second association study with said case group and said control group using an individual genotyping methodology, thereby determining which of said associated alleles are significantly more abundant in said case group than said control group based on said second association study, wherein those of said associated alleles that are significantly more abundant in said case group than said control group based on said second association study are the validated associated alleles.

22. The method of claim 2, further comprising validating said associated alleles by performing a second association study with a second case group that exhibits the multifactorial trait and a second control group that does not exhibit the multifactorial trait, thereby determining which of said associated alleles are significantly more abundant in the second case group than the second control group, wherein those of said associated alleles that are significantly more abundant in the second case group than the second control group are the validated associated alleles.

23. The method of claim 2, further comprising determining a one of said at least one threshold value by a method comprising
   a) calculating a score for each member of said case group and said control group;
   b) selecting a series of risk cutoff values;
   c) computing a set of values for each of said series of risk cutoff values, wherein said set of values comprises at least one of a sensitivity, a specificity, a PPV, an NPV, an accuracy, a relative risk, an LR+ and an LR−;
   d) choosing a one of said series of risk cutoff values as said one of said at least one threshold value based on said set of values, thereby determining said one of said at least one threshold value.

24. The method of claim 23, wherein calculating a score for each member of said case group and said control group comprises
   a) determining a genotype for said each member at said plurality of biallelic polymorphic loci, wherein the genotype is selected from the group consisting of homozygous for an associated allele, heterozygous, and homozygous for an unassociated allele;
   b) assigning a value of zero to each of said polymorphic loci that has a genotype that is homozygous for an allele that is not the associated allele;
   c) assigning a value of one to each of said polymorphic loci that has a genotype that is heterozygous;
   d) assigning a value of two to each of said polymorphic loci that has a genotype that is homozygous for the associated allele;
   e) summing the values determined in steps a) through c) for all said polymorphic loci, thereby calculating a score for said each member of said case group and said control group.

25. The method of claim 23, wherein said selecting a series of risk cutoff values comprises identifying a highest score from the scores calculated for each member of said case group and said control group;
determining a risk cutoff range, wherein the range is from 1 to said highest score;
selecting a series of values from across the risk cutoff range, thereby selecting said series of risk cutoff values.

26. The method of claim 25, wherein said selecting said series of values from across the risk cutoff range comprises a method selected from the group consisting of
   selecting every value within the risk cutoff range;
   selecting every nth value within the risk cutoff range;
   dividing the risk cutoff range into percentages and selecting a value at every nth percent of the risk cutoff range;
   selecting a larger number of values from a middle portion of the risk cutoff range than from a top or bottom portion of the risk cutoff range; and
   selecting a larger number of values from a top or bottom portion of the risk cutoff range than from a middle portion of the risk cutoff range.

27. The method of claim 23, wherein for a given risk cutoff value said sensitivity is computed by determining a proportion of said members of said case group that have a score greater than said given risk cutoff value, wherein said proportion is the sensitivity for said given risk cutoff value.

28. The method of claim 23, wherein for a given risk cutoff value said specificity is computed by determining a proportion of said members of said control group that have a score equal to or less than said given risk cutoff value, wherein said proportion is the specificity for said given risk cutoff value.

29. The method of claim 23, wherein said determining said one of said at least one threshold value further comprises using prior clinical knowledge of at least one of said multifactorial trait and said individual.

30. The method of claim 29, wherein said prior clinical knowledge includes a severity of said multifactorial trait.

31. The method of claim 29, wherein said prior clinical knowledge includes a prevalence of said multifactorial trait.

32. The method of claim 23, wherein said determining said one of said at least one threshold value further comprises using a ROC curve based on said sensitivity and said specificity computed in c), wherein a graphical representation of said ROC curve is referred to as a plot.

33. The method of claim 32, wherein said determining said one of said at least one threshold value further comprises choosing said one of said at least one threshold value from a portion of said ROC curve that is nearest an upper left corner of said plot.

34. The method of claim 33, wherein said portion comprises about 20% of said ROC curve.

35. The method of claim 32, further comprising choosing as said one of said at least one threshold value a risk cutoff value corresponding to a data point on said ROC curve that is nearer an upper left corner of said plot than any other data point on said ROC curve, wherein each data point on said ROC curve corresponds to a different risk cutoff value.

36. The method of claim 32, further comprising
   a) determining a location on said ROC curve that is nearest an upper left corner of said plot and to determine a sensitivity and a specificity that correspond to said location;
   b) analyzing said scores for each member of said case group and said control group to identify a risk cutoff value whose sensitivity and specificity are nearest said sensitivity and specificity that correspond to said location, wherein said risk cutoff value whose sensitivity and specificity are nearest said sensitivity and specificity that correspond to said location is said one of said at least one threshold value.

37. The method of claim 23, wherein for a given risk cutoff value said relative risk is computed by a method comprising
   a) determining a percentage of said members of said case group that have a score that is at least as great as said given risk cutoff value;
   b) determining a percentage of said members of said control group that have a score that is at least as great as said given risk cutoff value; and
   c) dividing said percentage determined in a) by said percentage determined in b) to compute said relative risk.

38. The method of claim 37, further comprising calculating a risk that a given individual with a score equal to the given risk cutoff value will develop or exhibit said multifactorial trait by multiplying said relative risk by the prevalence of said multifactorial trait.

39. The method of claim 23, wherein for a given risk cutoff value said PPV is computed by dividing the number of members of said case group with a score higher than said given risk cutoff value by the number of members of said case group and said control group that have a score greater than said given risk cutoff value.

40. The method of claim 23, wherein for a given risk cutoff value said NPV is computed by dividing the number of members of said control group with a score lower than said given risk cutoff value by the number of members of said case group and said control group that have a score lower than said given risk cutoff value.

41. The method of claim 1, wherein said polymorphic loci are SNPs.

42. The method of claim 1, wherein said individual is selected from the group consisting of a mammal, a reptile, an amphibian, a fish, a bird, a crustacean, an insect, a plant, a bacterium, a virus, and an archaean.

43. The method of claim 1, wherein said individual is a human.

44. The method of claim 1, wherein said computing a score further comprises
   a) assigning a value of zero to each of said polymorphic loci that has a genotype that is homozygous for an allele that is not the associated allele;
   b) assigning a value of one to each of said polymorphic loci that has a genotype that is heterozygous;
   c) assigning a value of two to each of said polymorphic loci that has a genotype that is homozygous for the associated allele;
   d) summing the values determined in steps a) through c) for all of said polymorphic loci, thereby computing a score for said individual.

45. The method of claim 1, wherein said multifactorial trait is a disease.

46. The method of claim 45, further comprising taking measures to prevent said disease if said score is greater than a one of said at least one threshold value.

47. The method of claim 45, wherein said disease confers a known risk of an adverse response to a drug.

48. The method of claim 47, further comprising excluding said individual from treatment with said drug if said score is greater than a one of said at least one threshold value.

49. The method of claim 45, wherein said individual has a family history of said disease.

50. The method of claim 45, wherein said individual displays symptoms of said disease.

51. The method of claim 1, wherein said multifactorial trait is a response to a drug.

52. The method of claim 51, wherein said response is a lack of an efficacious response to said drug.

53. The method of claim 52 further comprising excluding said individual from treatment with said drug if said score is greater than a one of said at least one threshold value.

54. The method of claim 51, wherein said response is an adverse event caused by the administration of said drug.

55. The method of claim 54, further comprising excluding said individual from said administration of said drug if said score is greater than a one of said at least one threshold value.

56. The method of claim 51, wherein said response is an efficacious response to a generic drug, wherein said generic drug is in a drug class comprising at least one brand name drug, and wherein said individual's likelihood of having an efficacious response to said generic drug is used to determine whether said generic drug will be administered to said individual.

57. The method of claim 51, wherein said response is an efficacious response to a generic drug, wherein said generic drug is in a drug class comprising at least one brand name drug, and wherein said individual's likelihood of having an efficacious response to said generic drug is used to determine whether treatment with said brand name drug will be reimbursable.

58. The method of claim 1, wherein said comparison reveals that said score is greater than a one of said at least one threshold value and said individual is assessed to be likely to exhibit the multifactorial trait.

59. The method of claim 1, wherein said comparison reveals that said score is less than or equal to a one of said at least one threshold value and said individual is assessed to be unlikely to exhibit the multifactorial trait.

60. The method of claim 1, wherein said comparison reveals that said score is less than or equal to a first of said at least one threshold value and greater than a second of said at least one threshold value, further comprising using additional factors to determine an appropriate course of treatment for said individual.

61. The method of claim 60, wherein said additional factors include at least one factor from the group consisting of information regarding said multifactorial trait, information regarding said individual, information regarding potential treatment options, input from said individual, and input from a regulatory agency.

62. A diagnostic or prognostic assay comprising nucleic acid probes designed to detect the associated alleles of claim 1 in a biological sample.

63. The assay of claim 62, wherein said probes are bound to a solid substrate.

64. A method for assessing an individual's likelihood of developing or exhibiting a multifactorial trait comprising
   a) determining a genotype for said individual at a plurality of biallelic polymorphic loci, wherein each of said plurality has an associated allele and an unassociated allele, and further wherein the genotype is selected from the group consisting of homozygous for the associated allele, heterozygous, and homozygous for an unassociated allele, and further wherein said associated alleles and said unassociated alleles are identified by performing an association study with a case group that exhibits the multifactorial trait and a control group that does not exhibit the multifactorial trait, thereby determining a set of alleles of said polymorphic loci that are significantly more abundant in the case group than the control group, wherein said set of alleles are the associated alleles, and further wherein said case and said control groups are matched prior to performing the association study;

b) computing a score for said individual based on said genotypes determined in a), wherein said computing a score further comprises assigning a value of zero to each of said polymorphic loci that has a genotype that is homozygous for an allele that is not the associated allele; assigning a value of one to each of said polymorphic loci that has a genotype that is heterozygous; assigning a value of two to each of said polymorphic loci that has a genotype that is homozygous for the associated allele; and summing the values assigned to all of said polymorphic loci, thereby computing a score for said individual; and c) performing a comparison of the score to at least one threshold value, wherein said comparison is used to determine an appropriate course of treatment for said individual, wherein each of said at least one threshold value is determined by a method comprising calculating a score for each member of said case group and said control group; selecting a series of risk cutoff values; compiling information, wherein said information comprises at least one of a sensitivity, a specificity, a PPV, an NPV, an accuracy, a relative risk, an LR+, an LR−, clinical data regarding said multifactorial trait, clinical data regarding said individual, clinical data regarding potential treatment options, and input from at least one regulatory agency; choosing a one of said series of risk cutoff values as said each of said at least one threshold value based on said information, thereby determining said each of said at least one threshold value.

* * * * *